(12) United States Patent
Weng et al.

(10) Patent No.: US 6,691,042 B2
(45) Date of Patent: Feb. 10, 2004

(54) METHODS FOR GENERATING DIFFERENTIAL PROFILES BY COMBINING DATA OBTAINED IN SEPARATE MEASUREMENTS

(75) Inventors: Lee Weng, Bellevue, WA (US); Hongyue Dai, Bothell, WA (US)

(73) Assignee: Rosetta Inpharmatics LLC, Kirkland, WA (US)

( * ) Notice: Subject to any disclaimer, the term of this patent is extended or adjusted under 35 U.S.C. 154(b) by 0 days.

(21) Appl. No.: 09/898,559

(22) Filed: Jul. 2, 2001

(65) Prior Publication Data
US 2003/0078736 A1 Apr. 24, 2003

(51) Int. Cl.[7] ............... G01N 33/48; G01N 33/53; G06F 19/00; C12Q 1/68
(52) U.S. Cl. ............... 702/19; 435/6; 435/7.1; 702/20
(58) Field of Search .............. 435/6, 7.1; 702/19, 702/20

(56) References Cited

U.S. PATENT DOCUMENTS

| | | | |
|---|---|---|---|
| 5,291,498 A | 3/1994 | Jackson et al. | 371/40.1 |
| 5,414,719 A | 5/1995 | Iwaki et al. | 371/37.1 |
| 5,510,270 A | 4/1996 | Fodor et al. | |
| 5,539,083 A | 7/1996 | Cook et al. | |
| 5,545,522 A | 8/1996 | Van Gelder et al. | |
| 5,552,270 A | 9/1996 | Khrapko et al. | |
| 5,556,752 A | 9/1996 | Lockhart et al. | |
| 5,569,588 A | 10/1996 | Ashby et al. | |
| 5,578,832 A | 11/1996 | Trulson et al. | |
| 5,716,785 A | 2/1998 | Van Gelder et al. | |
| 5,777,888 A | 7/1998 | Rine et al. | |
| 5,800,992 A | 9/1998 | Fodor et al. | |
| 5,891,636 A | 4/1999 | Van Gelder et al. | |
| 5,965,352 A | 10/1999 | Stoughton et al. | |
| 6,023,586 A | 2/2000 | Gaisford et al. | 395/712 |
| 6,028,189 A | 2/2000 | Blanchard | |
| 6,040,138 A | 3/2000 | Lockhart et al. | |
| 6,090,550 A | 7/2000 | Collinge et al. | 435/6 |
| 6,132,997 A | 10/2000 | Shannon | |
| 6,141,657 A * | 10/2000 | Rothberg et al. | 707/6 |
| 6,218,122 B1 | 4/2001 | Friend et al. | |
| 6,271,002 B1 | 8/2001 | Linsley et al. | |
| 6,351,712 B1 | 2/2002 | Stoughton et al. | 702/19 |

FOREIGN PATENT DOCUMENTS

| | | |
|---|---|---|
| WO | WO 88/09810 | 12/1988 |
| WO | WO 90/11364 | 10/1990 |
| WO | WO 98/38329 | 9/1998 |
| WO | WO 98/41531 | 9/1998 |
| WO | WO 99/58708 | 11/1999 |
| WO | WO 99/58720 | 11/1999 |
| WO | WO 99/59037 | 11/1999 |
| WO | WO 99/66067 | 12/1999 |
| WO | WO 00/24936 | 5/2000 |
| WO | WO 00/39336 | 7/2000 |

OTHER PUBLICATIONS

U.S. patent application Ser. No. 09/222,596, Stoughton et al., filed Dec. 28, 1998.

(List continued on next page.)

*Primary Examiner*—Ardin H. Marschel
(74) *Attorney, Agent, or Firm*—Pennie & Edmonds LLP

(57) ABSTRACT

The invention provides methods for generating differential profiles having been subject to condition A vs. condition B (A vs. B) from data obtained in separately performed experimental measurements A vs. C and B vs. D. When C and D are the same, the invention provides methods for determination of systematic measurement errors or biases between different measurements carried out in different experimental reactions, i.e., cross-experiment errors or biases, using data measured for samples under the common condition and for removal or reduction of such cross-experiment errors. The invention further provides methods for generating differential profiles A vs. B from data obtained in single-channel measurements A and B.

46 Claims, 28 Drawing Sheets

OTHER PUBLICATIONS

U.S. patent application Ser. No. 09/364,751, Friend et al., filed Jul. 30, 1999.

U.S. patent application Ser. No. 09/561,487, Friend et al., filed Apr. 28, 2000.

U.S. patent application Ser. No. 60/309,067, Dai et al., filed Jul. 31, 2001.

U.S. patent application Ser. No. 60/286,588, Dai et al., filed Apr. 26, 2001.

U.S. patent application Ser. No. 60/253,641, Ziman et al., filed Nov. 28, 2000.

U.S. patent application Ser. No. 60/227,966, Shoemaker et al., filed Aug. 25, 2000.

U.S. patent application Ser. No. 60/084,742, Friend et al., filed May 8, 1998.

Anderson et al., 1994, "Involvement of the protein tyrosine kinase p56lck in T cell signaling and thymocyte development", Adv Immunol 56:151–178.

Bass, 2000, "Double–Stranded RNA as a Template for Gene Silencing", Cell 101: 235–238.

Belshaw et al, 1996, "Controlling protein association and subcellular localization with a synthetic ligand that induces heterodimerization of proteins", Proc Natl Acad Sci U S A 93: 4604–4607.

Bernoist and Chamabon, 1981, "In vivo sequence requirements of the SV40 early promotor region", Nature 290: 304–310.

Blanchard et al., 1996, "Sequence to array: probing the genome's secrets", Nature Biotechnol 14:1649.

Blanchard et al., 1996, "High–density oligonucleotide arrays", Biosensors and Bioelectronics 11:687–690.

Blanchard, 1998, *Synthetic DNA Arrays in Genetic Engineering*, vol. 20, J.K. Setlow, Ed., pp 111–123.

Brinster et al., 1982, "Regulation of metallothionein—thymidine kinase fusion plasmids injected into mouse eggs", Nature 296:39–42.

Cech, 1987, "The chemistry of self–splicing RNA and RNA enzymes", Science 236: 1532–1539.

Chait, 1996, "Trawling for proteins in the post–genome era," Nature Biotechnology 14:1544.

Chirgwin et al, 1979, "Isolation of biologically active ribonucleic acid from sources enriched in ribonuclease", Biochemistry 18: 5294–5299.

Cotten et al, 1989, "Ribozyme mediated destruction of RNA in vivo", EMBO J. 8: 3861–3866.

Crollius et al., 2000, "Estimate of human gene number provided by genome–wide analysis using Tetraodon nigroviridis DNA sequence," Nature Genetics 25: 235–238.

DeRisi et al., 1996, "Use of a cDNA microarray to analyze gene expression patterns in human cancer," Nature Genetics 14:457–460.

DeRisi et al., 1997, "Exploring the metabolic and genetic control of gene expression on a genomic scale," Science 278:680–686.

Egholm et al., 1993, "PNA hybridizes to complementary oligonucleotides obeying the Watson–Crick hydrogenbonding rules," Nature 365: 566–568.

Ewing et al., 2000, "Analysis of expressed sequence tags indicates 35,000 human genes," Nature Genetics 25: 232–234.

Ferguson et al., 1996, "A fiber–optic DNA biosensor microarray for the analysis of gene expression", Nature Biotechnology 14: 1681–1684.

Fire et al., 1998, "Potent and specific genetic interference by double–stranded RNA in *Caenorhabditis elegans*", Nature 391: 806–811.

Fodor et al., 1991, "Light–directed, spatially addressable parallel chemical synthesis", Science 251: 767–773.

Froehler et al., 1986, "Synthesis of DNA via deoxynucleoside H–phosphonate intermediates", Nucleic Acids Res 14: 5399–5407.

Gautier et al, 1987, "Alpha–DNA. IV: Alpha–anomeric and beta–anomeric tetrathymidylates covalently linked to intercalating oxazolopyridocarbazole. Synthesis, physicochemical properties and poly (rA) binding", Nucleic Acids Res 15: 6625–6641.

Gibson, 1996, "Antisense approaches to the gene therapy of cancer—'Recnac'", Cancer Metastasis Rev. 15: 287–299.

Goffeau et al., 1996, "Life with 6000 genes", Science 274: 546–567.

Good et al., 1997, "Expression of small, therapeutic RNAs in human cell nuclei", Gene Therapy 4: 45–54.

Gossen et al., 1995, "Tight control of gene expression in mammalian cells by tetracycline–responsive promoters", Proc. Natl. Acad. Sci. USA 89: 5547–5551.

Grant, 1999, "Dissecting the Mechanisms of Posttranscriptional Gene Silencing: Divide and Conquer," Cell 101: 25–33.

Grassi and Marini, 1996, "Ribozymes: structure, function and potential therapy for dominant genetic disorders", Annals Medicine 28: 499–510.

Guo et al., 1995, "par–1, a Gene Required for Establishing Polarity in *C. elegans* Embryos, Encodes a Putative Ser/Thr Kinase That Is Asymmetrically Distributed," Cell 81: 611–620.

Hanke, 1996, "Discovery of a novel, potent, and Src family–selective tyrosine kinase inhibitor. Study of Lck– and FynT–dependent T cell activation", J Biol Chem 271: 695–701.

Haseloffet al., 1988, "Simple RNA enzymes with new and highly specific endoribonuclease activities", Nature 334: 585–591.

Hoffmann et al., 1996, "Rapid retroviral delivery of tetracycline–inducible genes in a single autoregulatory cassette", Proc Natl Acad Sci USA 93: 5185–5190.

Inoue et al., 1987, "Synthesis and hybridization studies on two complementary nona(2'–O–methyl)ribonucleotides", Nucleic Acids Res 15:6131–6148.

Inoue et al., 1987, "Sequence–dependent hydrolysis of RNA using modified oligonucleotide splints and RNase H", FEBS Lett 215: 327–330.

Koizumi et al, 1988, "Construction of a series of several self–cleaving RNA duplexes using synthetic 21–mers", FEBS Lett. 228: 228–230.

Koizumi et al, 1988, "Cleavage of specific sites of RNA by designed ribozymes", FEBS Lett. 239: 285–288.

Kricka, 1992, *Nonisotopic DNA Probe Techniques*, Academic Press, San Diego, CA.

Lematire et al., 1987, "Specific antiviral activity of a poly(L–lysine)–conjugated oligodeoxyribonucleotide sequence complementary to vesicular stomatitis virus N protein mRNA initiation site", Proc Natl Acad Sci USA 84: 648–652.

Letsinger et al., 1989, "Cholesteryl–conjugated oligonucleotides: synthesis, properties, and activity as inhibitors of replication of human immunodeficiency virus in cell culture", Proc Natl Acad Sci USA 86: 6553–6556.

Lockhart et al., 1996, "Expression monitoring by hybridization to high–density oligonucleotide arrays", Nature Biotechnology 14:1675–1680.

Marton et al., 1998, "Drug target validation and identification of secondary drug target effects using DNA microarrays," Nature Medicine 4(11):1293–1301.

Maskos and Southern, 1992, "Oligonucleotide hybridizations on glass supports: a novel linker for oligonucleotide synthesis and hybridization properties of oligonucleotides synthesised in situ", Nucleic Acids Res 20: 1679–1684.

McBride et al., 1983, "An investigation of several deoxynucleoside phosphoramidites useful for synthesizing deoxyoligonucleotides", Tetrahedron Lett 24: 245–248.

McGall et al, 1996, "Light–Directed synthesis of high–density oligonucleotide arrays using semiconductor photoresists," Proc. Natl. Acad. Sci. U.S.A. 93: 13555–13560.

McCormack et al., 1997, "Direct analysis and identification of proteins in mixtures by LC/MS/MS and database searching at low–femtomole level", Anal. Chem. 69:767–776.

Nguyen et al., 1995, "Differential gene expression in the murine thymus assayed by quantitative hybridization of arrayed cDNA clones", Genomics 29: 207–216.

No et al., 1996, "Ecdysone–inducible gene expression in mammalian cells and transgenic mice", Proc. Natl. Acad. Sci. USA 93(8): 3346–3351.

Paulas et al, 1996, "Self–contained, tetracycline–regulated retroviral vector system for gene delivery to mammalian cells", J Virol 70: 62–67.

Pease et al., 1994, "Light–generated oligonucleotide arrays for rapid DNA sequence analysis", Proc Natl Acad Sci USA 91(11): 5022–5026.

Petcherski et al, 2000, "LAG–3 is a putative transcriptional activator in the *C. elegans* Notch Pathway," 405: 364–368.

Pettitt et al., 1996, "cdh–3, a gene encoding a member of the cadherin superfamily, functions in epithelial cell morphogenesis in *Caenorhabditis elegans*", Development 122: 4149–4157.

Ramirez–Solis et al., 1993, "Gene targeting in embryonic stem cells", Methods Enzymol 225: 855–878.

Sarin et al., 1988, "Inhibition of acquired immunodeficiency syndrome virus by oligodeoxynucleoside methylphosphonates", Proc Natl Acad Sci USA 85: 7448–7451.

Sarver et al., 1990, "Ribozymes as potential anti–HIV–1 therapeutic agents", Science 247: 1222–1225.

Schena et al., 1995, "Quantitative monitoring of gene expression patterns with a complementary DNA microarray", Science 270:467–470.

Schena et al., 1996, "Parallel human genome analysis; microarray–based expression of 1000 genes," *Proc. Natl. Acad. Sci. USA* 93:10614–10619.

Shalon et al., 1996, "A DNA microarray system for analyzing complex DNA samples using two–color fluorescent probe hybridization", Genome Res 6(7): 639–645.

Spencer, 1996, "Creating conditional mutations in mammals", Trends Genet 12: 181–187.

Spradling et al., 1995, "Gene disruptions using P transposable elements: an integral component of the Drosophila genome project", Proc Natl Acad Sci USA 92: 10824–10830.

Stein et al, 1988, "Physicochemical properties of phosphorothioate oligodeoxynucleotides", Nucleic Acids Res 16: 3209–3221.

Straus et al, 1992, "Genetic evidence for the involvement of the lck tyrosine kinase in signal transduction through the T cell antigen receptor", Cell 70: 585–593.

Thomas et al, 1987, "Site–directed mutagenesis by gene targeting in mouse embryo–derived stem cells", Cell 51: 5003–512.

Tijessen, 1993, *Hybridization With Nucleic Acid Probes*, Elsevier Science Publishers.

Van der Krol et al, 1988, Modulation of eukaryotic gene expression by complementary RNA or DNA sequences. Biotechniques 6: 958–976.

Van Trees, 1968, *Detection, Estimaton, and Modulation Theory*, vol. 1.

Wagner et al, 1981, "Nucleotide sequence of the thymidine kinase gene of herpes simplex virus type 1", Proc. Natl. Acad. Sci. USA 78: 1441–1445.

Yamamoto et al, 1980, "Identification of a functional promoter in the long terminal repeat of *Rous sarcoma* virus", Cell 22: 787–797.

Zon, 1988, "Oligonucleotide analogues as potential chemotherapeutic agents", Pharm Res 5: 539–549.

* cited by examiner

METHODS FOR GENERATING DIFFERENTIAL PROFILES BY COMBINING DATA OBTAINED IN SEPARATE MEASUREMENTS

1. FIELD OF THE INVENTION

The present invention relates to methods for generating differential expression profiles by combining expression data obtained in separate microarray measurements. The invention also relates to methods for determination and removal or reduction of systematic measurement biases between different microarrays.

2. BACKGROUND OF THE INVENTION

DNA array technologies have made it possible to monitor the expression level of a large number of genetic transcripts at any one time (see, e.g., Schena et al., 1995, *Science* 270:467–470; Lockhart et al., 1996, *Nature Biotechnology* 14:1675–1680; Blanchard et al., 1996, *Nature Biotechnology* 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, *Nature Genetics* 14:457–460; Shalon et al., 1996, *Genome Res.* 6:689–645; Schena et al., 1995, *Proc. Natl. Acad. Sci. U.S.A.* 93:10539–11286; and Duggan et al., *Nature Genetics* Supplement 21:10–14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; McGall et al., 1996, *Proc. Natl. Acad. Sci. U.S.A.* 93:13555–13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., U.S. patent application Ser. No. 09/364,751, filed on Jul. 30, 1999; and Friend et al., U.S. patent application Ser. No. 09/561,487, filed on Apr. 28, 2000).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. patent application Ser. No. 09/334,328 (filed on Jun. 16, 1999).

The various characteristics of this analytic method make it particularly useful for directly comparing the abundance of mRNAs present in two cell types. For example, an array of cDNAs was hybridized with a green fluor-tagged representation of mRNAs extracted from a tumorigenic melanoma cell line (UACC-903) and a red fluor-tagged representation of mRNAs was extracted from a nontumorigenic derivative of the original cell line (UACC-903 +6). Monochrome images of the fluorescent intensity observed for each of the fluors were then combined by placing each image in the appropriate color channel of a red-green-blue (RGB) image. In this composite image, one can see the differential expression of genes in the two cell lines. Intense red fluorescence at a spot indicates a high level of expression of that gene in the nontumorigenic cell line, with little expression of the same gene in the tumorigenic parent. Conversely, intense green fluorescence at a spot indicates high expression of that gene in the tumorigenic line, with little expression in the nontumorigenic daughter line. When both cell lines express a gene at similar levels, the observed array spot is yellow.

In some cases, visual inspection of such results is sufficient to identify genes which show large differential expression in the two samples. A more thorough study of the changes in expression requires the ability to discern quantitatively changes in expression levels and to determine whether observed differences are the result of random variation or whether they are likely to reflect changes in the expression levels of the genes in the samples. Assuming that DNA products from two samples have an equal probability of hybridizing to the probes, the intensity measurement is a function of the quantity of the specific DNA products available within each sample. Locally (or pixelwise), the intensity measurement is also a function of the concentration of the probe molecules. On the scanning side, the fluorescent light intensity also depends on the power and wavelength of the laser, the quantum efficiency of the photomultiplier tube, and the efficiency of other electronic devices. The resolution of a scanned image is largely determined by processing requirements and acquisition speed. The scanning stage imposes a calibration requirement, though it may be relaxed later. The image analysis task is to extract the average fluorescence intensity from each probe site (e.g., a cDNA region).

The measured fluorescence intensity for each probe site comes from various sources, e.g., background, cross-hybridization, hybridization with sample 1 or sample 2. The average intensity within a probe site can be measured by the median image value on the site. This intensity serves as a measure of the total fluors emitted from the sample mRNA targets hybridized on the probe site. The median is used as the average to mitigate the effect of outlying pixel values created by noise.

Typically, in a two-color microarray gene expression experiment, the experiment sample is labeled in one dye color (Cy5, red) and the control sample is labeled in a different color (Cy3, green). The two samples are mixed and hybridized to a micro-array slide. After hybridization, the expression intensity is measured with a laser scanner of two different colors. The experiment is conducted in a biology laboratory (wet lab). To obtain the expression profile, we compute the logarithmic ratio of the two measured intensities (red and green).

There are two types of biases (errors) that may affect the accuracy of the ratio estimation, inter-slide bias and color bias. Inter-slide bias is the difference between two separated slides. The two-color technique avoids the inter-slide error by running the experiment in a single slide. But different dyes can cause difference between the two intensity measurements, so that the ratio is biased. To overcome this color bias problem, the experiment can be run twice with reversed flourescent dye labeling from one to the other. The two expression ratios are then combined to cancel out the color bias. A method for calculating individual errors associated with each measurement made in repeated microarray experiments was also developed. The method offers an approach for minimizing the number of times a cellular constituent quantification experiment must be repeated in order to produce data that has acceptable error levels and for combining data generated in repeats of a cellular constituent quantification experiment based on rank order of up-regulation or down-regulation. See, e.g., Stoughton et al., U.S. patent application Ser. No. 09/222,596 (filed on Dec. 28, 1998).

However, it is often desirable to know without actually running the experiment in the lab the difference of expression levels of genes between samples under two different conditions, such as condition A vs. condition B (A vs. B), when only separately measured experimental data A vs. C and B vs. D are available. There is therefore a need for methods for generating differential profiles, such as A vs. B, from separately measured data, such as A vs. C and B vs. D. In particular, because of the systematic measurement errors resulted from variations between two separate experiments and thus between the two separately measured data, there is a need for methods that make use of experimental data for estimating and reducing such systematic errors.

Discussion or citation of a reference herein shall not be construed as an admission that such reference is prior art to the present invention.

3. SUMMARY OF THE INVENTION

The invention provides methods for generating a differential profile A vs. B from measured data obtained under condition A vs. condition C (A vs. $C_A$) and condition B vs. condition C (B vs. $C_B$) measured in two separate experimental reactions. In the methods of the invention, the systematic measurement error or bias between the two different experiments, i.e., cross-experiment errors or biases, is estimated and removed using the data measured with the samples having been subject to the common condition, e.g., condition C. Specifically, a same-type (ST) differential profile $C_A$ vs. $C_B$ is formed using the two sets of separately measured data of sample having been subject to condition C. The inter-slide bias or error is then corrected by making use of this ST profile. In a preferred embodiment, the invention provides a method for generating an error-corrected differential profile A vs. B from sets of data A, B, $C_A$, and $C_B$, comprising (a) calculating a first differential profile A vs. B; (b) determining a systematic cross-experiment error by a method comprising calculating a reference differential profile $C_A$ vs. $C_B$; and (c) generating a second differential profile A vs. B by a method comprising correcting said first differential profile A vs. B using said determined systematic cross-experiment error; wherein said data set A, B, $C_A$ or $C_B$ comprises respectively data set {A(i)}, {B(i)}, {$C_A$(i)} or {$C_B$(i)} representing measurements of a plurality of different cellular constituents measured in a sample, said sample having been subject to a respective condition A, B, C or C, wherein i=1, 2, . . . , N is the index of measurements of cellular constituents, N being the total number of measurements; wherein data sets A and $C_A$ are measured in the same experimental reaction, and data sets B and $C_B$ are measured in the same experimental reaction; and wherein said second differential profile is taken as said error-corrected differential profile A vs. B. In the methods of the invention, inter-slide error is estimated statistically by C vs. C from a plurality of data points, e.g., array spots. Therefore, in embodiments of the invention, the total number of data points N for each data set used in the methods of the invention is preferably at least 100, more preferably at least 1000, even more preferably at least 10,000. In some embodiment, N is smaller than the total number of spots in the array. In some other embodiments, a data set can contain more than one measurement of the same cellular constituent. For example, a data set of measured levels of gene expression can contain the expression level of a gene measured by two or more different probes for the gene in a microarray. Preferably, the methods are used to generate differential profile A vs. B when both $C_A$ and $C_B$ are labeled with the same fluorophore. However, the methods can also be used to generate differential profile A vs. B when $C_A$ and $C_B$ are labeled with different fluorophores. In such embodiments, it is preferable that the fluorophore bias between $C_A$ and $C_B$ are removed before used in generating the ST profile $C_A$ vs. $C_B$. More preferably, the methods are used to generate differential profile A vs. B when A and B are labeled with a first fluorophore and $C_A$ and $C_B$ are labeled with a second fluorophore which is different from the first fluorophore.

In one embodiment, the inter-slide bias is removed by subtracting the ST log ratio $C_A$ vs. $C_B$ from the log ratio A vs. B. The subtraction is carried out by minimizing an objective function, i.e., a log-ratio-error normalized log-ratio difference weighted by a factor w, for the inter-slide error minimization process. In another embodiment, the inter-slide bias is removed by subtracting the ST arithmetic difference $C_A$ vs. $C_B$, i.e., $C_B-C_A$, from the arithmetic difference A vs. B. The subtraction, including scaling of the ST profile, is carried out by a method similar to the method for subtraction of log(ratio). In still another embodiment, the inter-slide bias is removed by subtracting the ST ratio $C_A$ vs. $C_B$, i.e., $C_B/C_A$, from the ratio A vs. B. The subtraction, including scaling of the ST profile, is carried out by a method similar to the method for subtraction of log(ratio).

In preferred embodiments, the generated expression profile A vs. B are further corrected for fluorophore bias. As described, supra, the two-color fluorescent hybridization process introduces bias into the profile analysis because each species of mRNA that is labeled with fluorophore has a bias in its measured color ratio due to interaction of the fluorescent labeling molecule (fluorophore) with either the reverse transcription of the mRNA or with the hybridization efficiency or both. Such a bias is also present in the generated expression profile A vs. B if samples under conditions A and B are labeled with different fluorophores. Thus, in one embodiment, if the fluor-reversed profile B vs. A is also generated, the fluorophore bias is removed by combining the pair of fluor-reversed profiles using any method known in the art.

The invention also provides methods for generating differential expression profile $A(T_1)$ vs. $A(T_2)$ from data measured at different hybridization times $T_1$ and $T_2$, i.e., different lengths of hybridization durations, in two separate measurements, thereby comparing expression data measured at the two hybridization times. In one embodiment, a differential expression profile $A(T_1)$ vs. $A(T_2)$ is generated from data sets $A(T_1)$ and $A(T_2)$ measured in single-channel experiments of A at hybridization times $T_1$ and $T_2$. In another embodiment, a differential expression profile $A(T_1)$ vs. $A(T_2)$ is generated from $A(T_1)$ vs. $C(T_1)$ and $A(T_2)$ vs. $C(T_2)$ measured in two separate two-channel experiments of A vs. C at hybridization times $T_1$ and $T_2$. Such methods are useful when changes in hybridization levels in time are to be determined, e.g., in methods in which hybridization kinetics is used for distinguishing hybridization specificity at different hybridization time. In preferred embodiments, the first hybridization level can be measured at between 1 to 10 hours, whereas the second hybridization time can be measured at about 2, 4, 6, 10, 12, 16, 18, 48 or 72 times as long as the first hybridization time. The invention thus provides a method for correcting any systematic errors that may arise between measurements carried out at different hybridization times.

In another embodiment, the invention provides a method for controlling the quality of microarray slide production process. The method is based on comparing two-channel measured data of samples under the same condition, e.g., C vs. C. In the method, one good quality slide is selected to serve as a standard. A second microarray slide is then randomly selected from a batch of production slide. Two identical same-type virtual experiments C vs. C for both slides are then generated. A quantitative production quality control process is established by first computing a correlation coefficient using the intensity ratio of the first virtual experiment (C vs. C with color label 1) and the intensity ratio of the second virtual experiment (C vs. C with color label 2) by an inter-slide correlation method, and then judging the quality of microarray slides by using a predetermined range of correlation coefficient. For example, the range of acceptable correlation coefficient can be set to be between −0.5 and 0.5.

The invention also provides methods for generating differential profiles using data from two separate single channel measurements, e.g., measurements from two microarray slides. In one embodiment, an expression profile A vs. B is generated by combining data from two measured single-channel data A and B. In another embodiment, an expression profile A vs. B is generated by combining single-channel data A and B picked up from the separately measured two-channel data A vs. C and B vs. D. In still another embodiment, an expression profile A vs. B is generated by combining single-channel data A and B picked up from two separately measured N-channel data, one containing A and one containing B. In preferred embodiments, data A and B are from channels of the same color in two different slides. Measurement errors in the two channels are removed by removing the additive noise in both channels. When A and B are measured in channels of different colors, color bias is also removed. In a preferred embodiment, the invention provides a method for generating a differential profile A vs. B from data sets A and B, comprising (a) determining mean background noise levels Abkg and Bbkg, and background noise residue ABres, from measured background noise levels in data sets A and B, respectively; (b) calculating noise-removed data sets A and B, respectively, by a method comprising (b1) removing said mean background noise level from said data sets A and B, and (b2) removing said background noise residue from said data sets A and B, respectively; and (c) generating said differential profile A vs. B from said noise-removed data sets A and B; wherein said data set A or B comprises respectively data set $\{A(i), A_{bkg}(i)\}$ or $\{B(i), B_{bkg}(i)\}$ representing measurements of a plurality of different cellular constituents in a sample, said sample having been subject to condition A or B, respectively; wherein $A_{bkg}(i)$ or $B_{bkg}(i)$ is said measured background noise level of measurement of cellular constituent i in said data set A or B, respectively; and wherein i=1, 2, ..., N is the index of measurements of cellular constituents, N being the total number of measurements. In some embodiments, the procedure for removing the background noise residue from data sets A and B is carried out once. In preferred embodiments, the procedure is repeated several times, such as 5, 10, or 20 times, to further reduce any remaining residuals. In one embodiment, the sample having been subject to condition A and the sample having been subject to condition B are labeled with the same fluorophore. In another embodiment, the sample having been subject to condition A is labeled with a first fluorophore and the sample having been subject to condition B is labeled with a second fluorophore, and the second fluorophore is different from the first fluorophore.

The invention also provides a computer system for carrying out the method of the invention of generating a differential profile, said computer system comprising a processor, and a memory coupled to said processor and encoding one or more programs, wherein said one or more programs cause the processor to carry out any of the method of the present invention.

The invention also provides a computer program product for use in conjunction with the computer system of the invention having a processor and a memory connected to the processor, said computer program product comprising a computer readable storage medium having a computer program mechanism encoded thereon, wherein said computer program mechanism may be loaded into the memory of said computer and cause said computer to carry out any of the method of present invention.

4. BRIEF DESCRIPTION OF FIGURES

Figure 3:
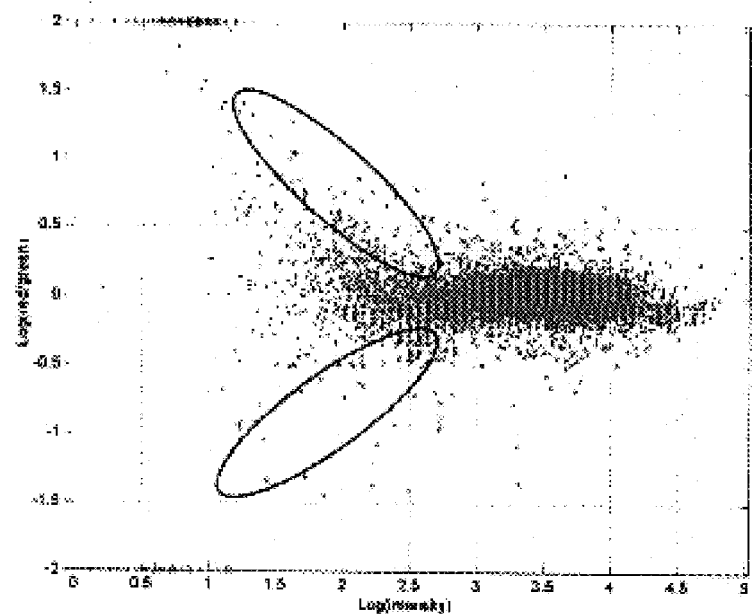
FIG. 3 illustrates an exemplary profile showing false signature (x) with under-estimated additive noise variance.
Figure 4:
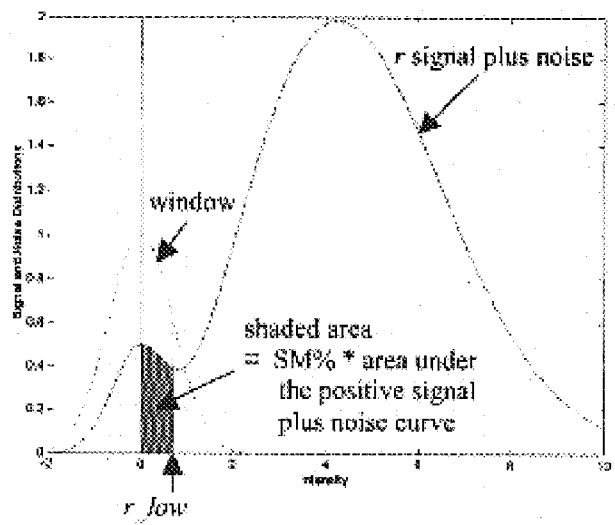

FIG. 4 shows method of defining the width of the weighting window. FIG. 4 is a conceptual plot of the r intensity distribution after background subtraction defined in Eq. 8a and Eq. 8b. Although the background offset level has been removed, the additive background noise fluctuation still remains, which is conceptually shown as a small bump in the distribution around zero intensity. Parameter SM % is experimentally defined to achieve the best balance of the "fish tail" in the left side of signature plots in FIG. 2. If SM % is too small or too large, the "fish tail" will not be properly balanced as the correct example shown in FIG. 3. Shown in FIG. 4, for a given r intensity distribution (r signal plus noise) and a given SM %, low r is the intensity level that makes the area between zero and the level under the distribution curve equal to SM % times the area under the curve at left side of the zero intensity.

Figure 5:
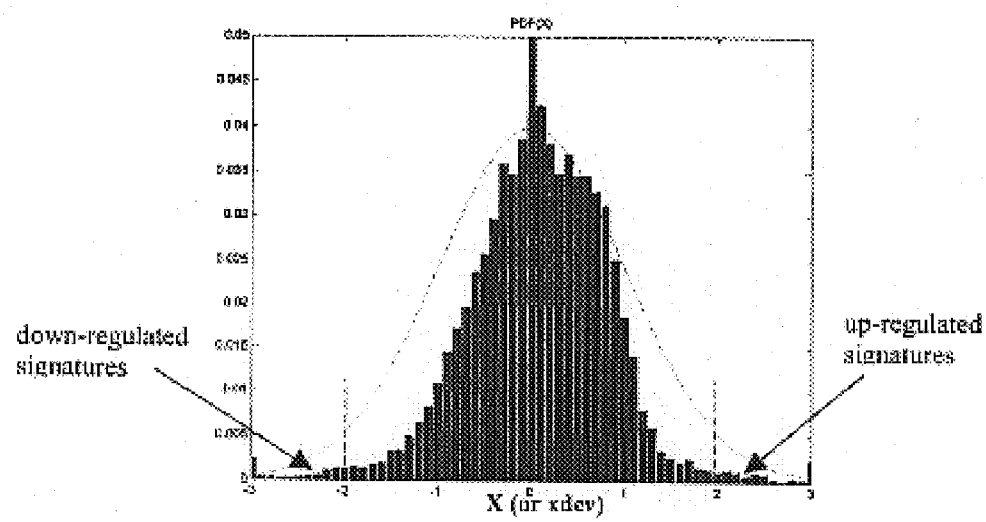

FIG. 5 illustrates a probability density function of the normalized intensity difference X, i.e., xdev.

Figure 6:
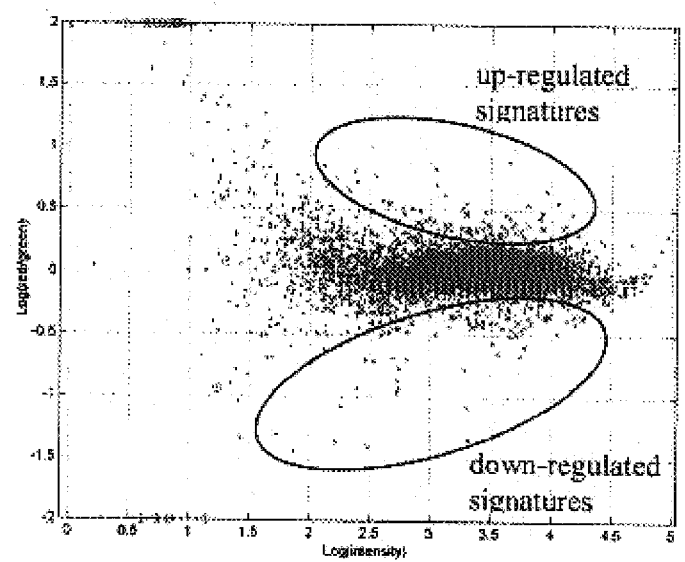

FIG. 6 shows an exemplary log intensity ratio plot. Signatures are marked by "x" (p=0.05). Data points marked by "o" are bad spots which have areas less than 40%.

Figure 7:
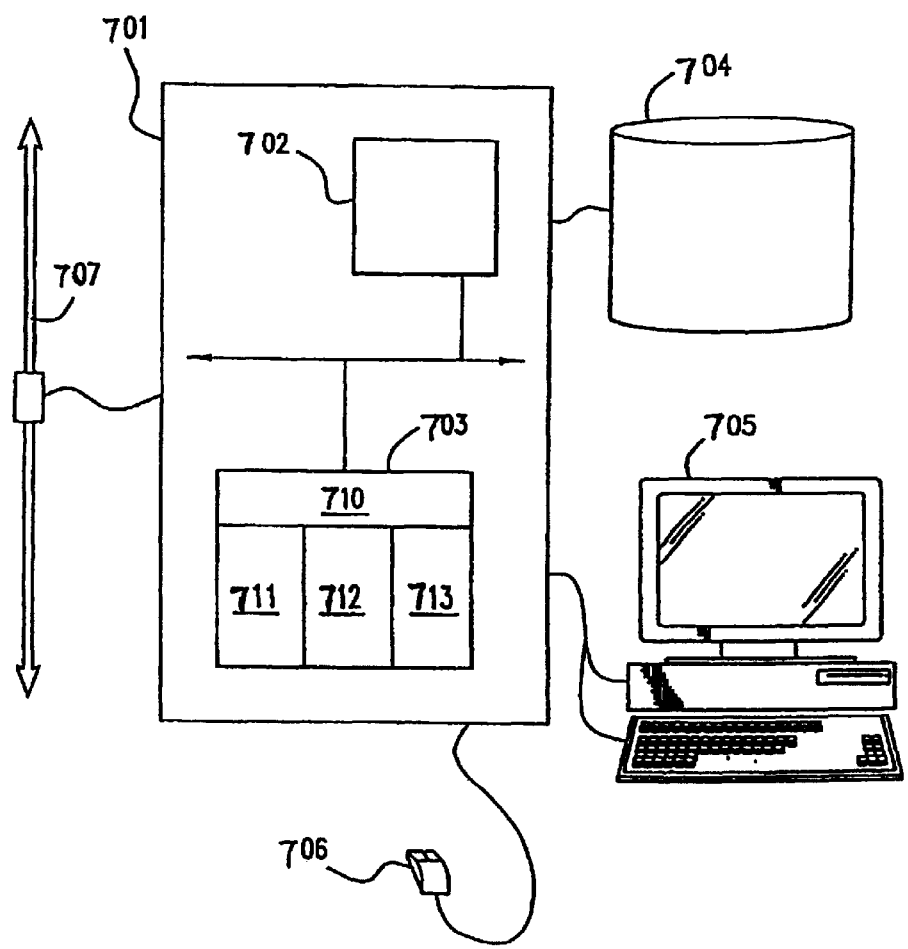

FIG. 7 illustrates an exemplary embodiment of a computer system useful for implementing the methods of this invention.

Figure 8:
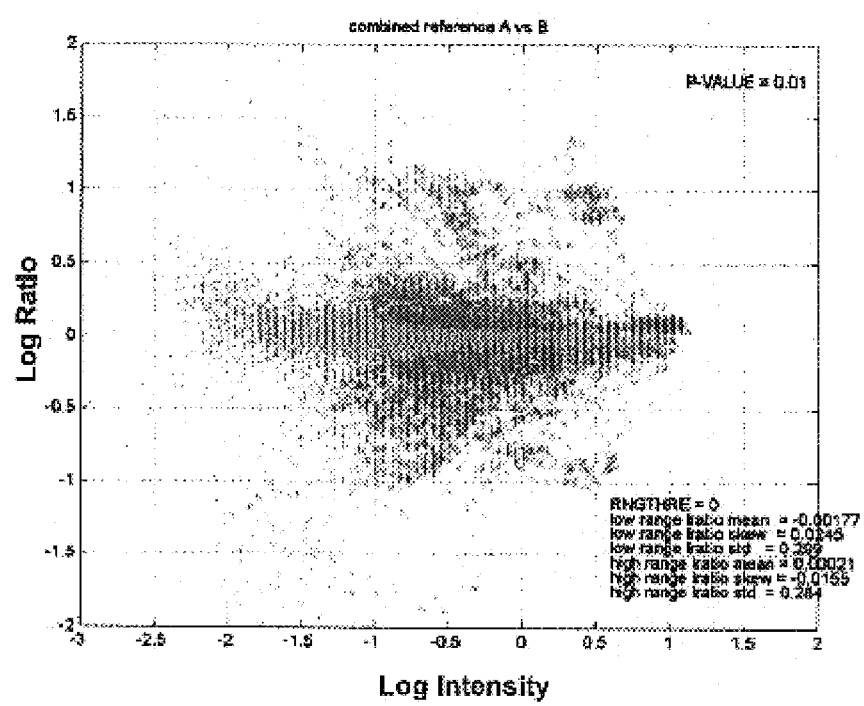

FIG. 8 is a log-ratio plot of the standard reference. Up- or down-regulated spots are marked in "x" for P-value 0.01. When computing the P-value, the 5-pair combined parameter xdev is divided by $\sqrt{5}$ to make the reference comparable to the result from a single-pair experiment (four channels of data from two slides) or an equivalent single-pair estimation (four channels of data from four slides)

Figure 9A:
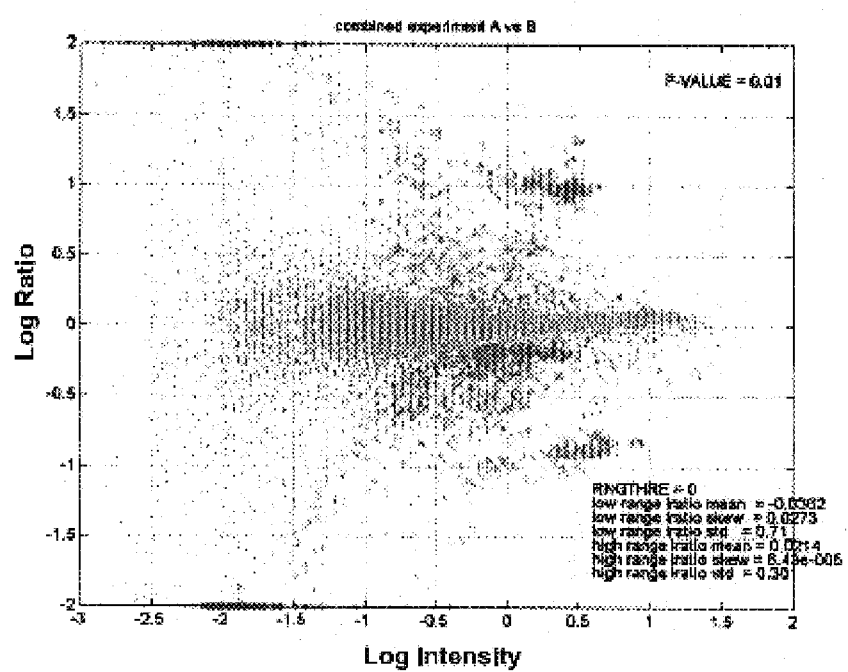
Figure 9B:
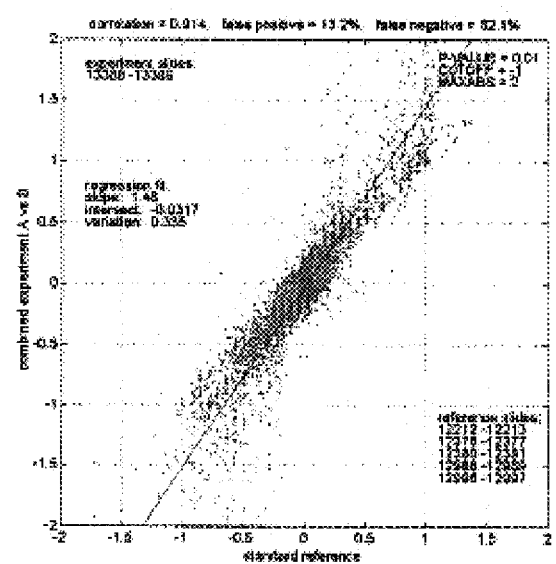

FIG. 9A is a log-ratio plot of a combined experiment A vs. B. FIG. 9B is a correlation plot of this combined experiment to the reference, where only those spots having log intensity higher than −1 are shown. Correlation is computed on the set of signature union from both the experiment and the reference. False positive is the percentage of number of spots that are signatures in the experiment but not signatures in the reference over the total number of signatures in the experiment. False negative is the percentage of number of spots that are not signatures in the experiment but signatures in the reference over the total number of signatures in the reference.

Figure 10A:
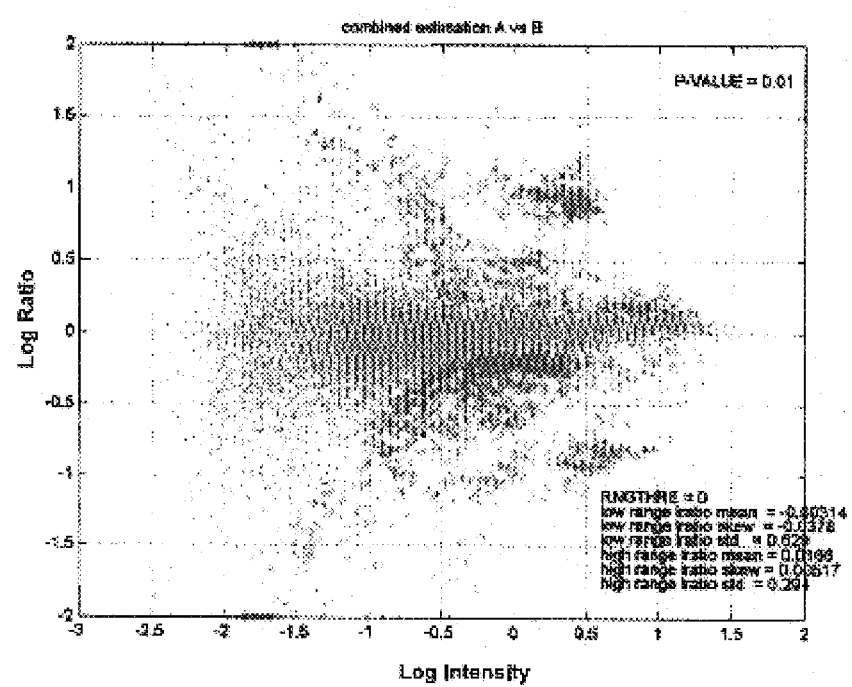
Figure 10B:
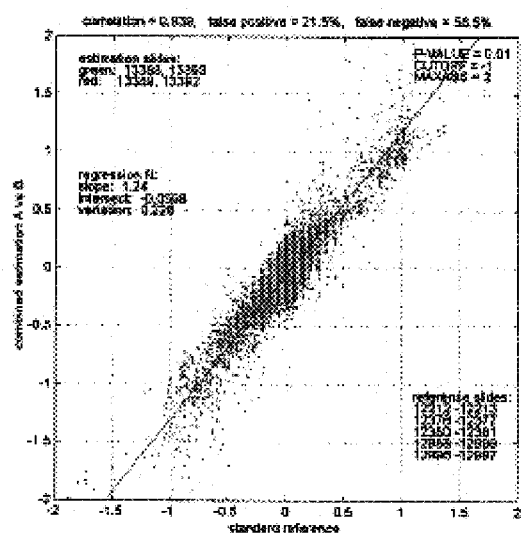

FIGS. 10A–10B show the results of a combined estimation. Both ratio plots of the experiment and the estimation are very similar to the reference. Signatures of both correlate well with the reference. But the estimation has a little higher false positive, which is caused by inter-slide bias.

Figure 11:
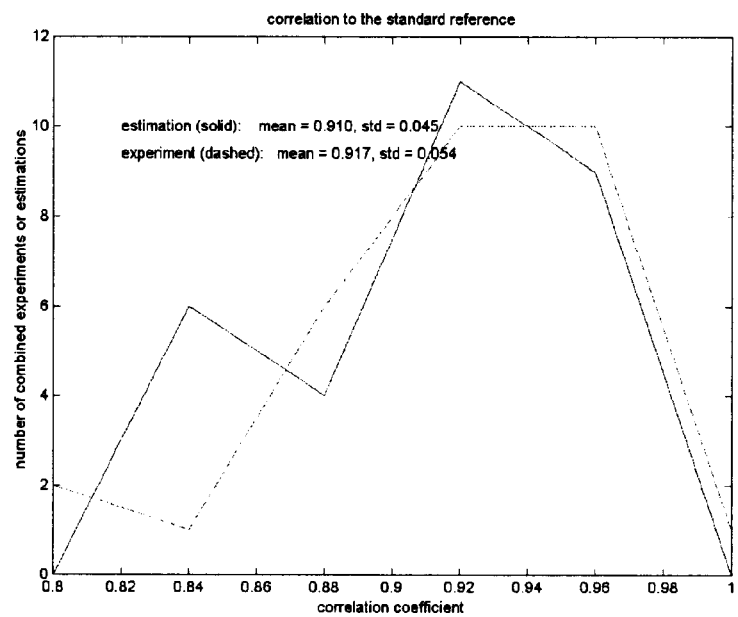

FIG. 11 displays the histograms of the correlation coefficients between the combined experiments or the combined estimations to the standard reference. A null hypothesis is formed by subtracting the experiment correlation coefficient from the estimation coefficient. A t-test is performed on the null hypothesis. The result p-value is 0.47, which indicates there is not statistical difference between the correlation coefficients of the experiment and the estimation for these 60 slides.

Figure 12:
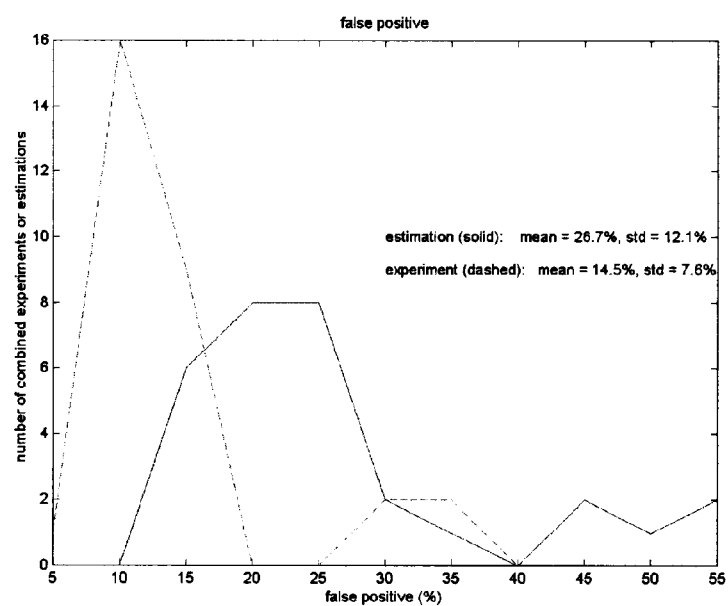

FIG. 12 displays the histograms of the false positive of the combined experiments and the combined estimations. A null hypothesis is formed by subtracting the experiment false positive from the false positive of the estimation. A t-test is performed on this null hypothesis. The result p-value is 1.38e-7 and the confidence interval is [+8.6, +15.8] for p-value=0.05, which indicates that the false positives of the estimation is statistically significantly higher than the false positive of the experiment for these 60 slides.

Figure 13:
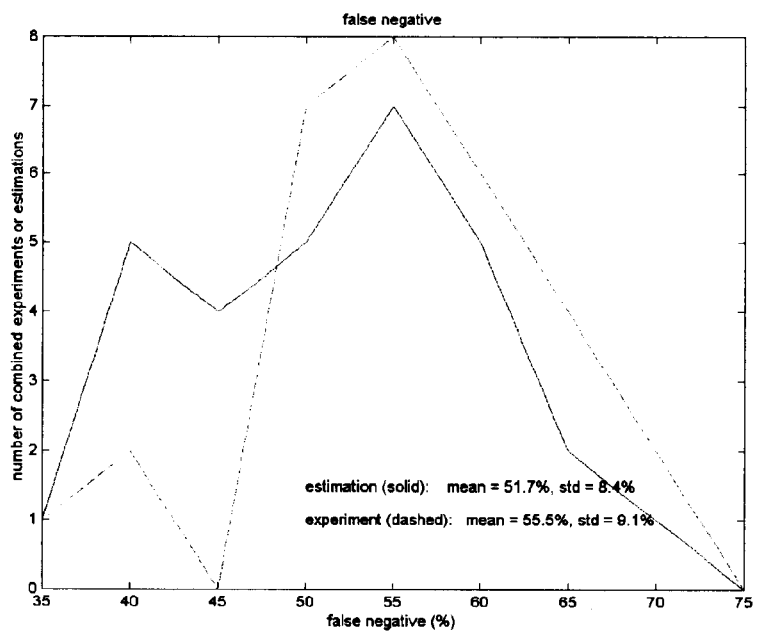

FIG. 13 shows the histograms of the false negative of the combined experiments and the combined estimations. A null hypothesis is formed by subtracting the experiment false negative from the false negative of the estimation. A t-test is performed on this null hypothesis. The result p-value is 0.01 and the confidence interval is [−6.5, −0.9] for p-value=0.05, which indicates that the false negative of the estimation is statistically significantly lower than the false negative of the real experiment for these 60 slides.

Figure 14:
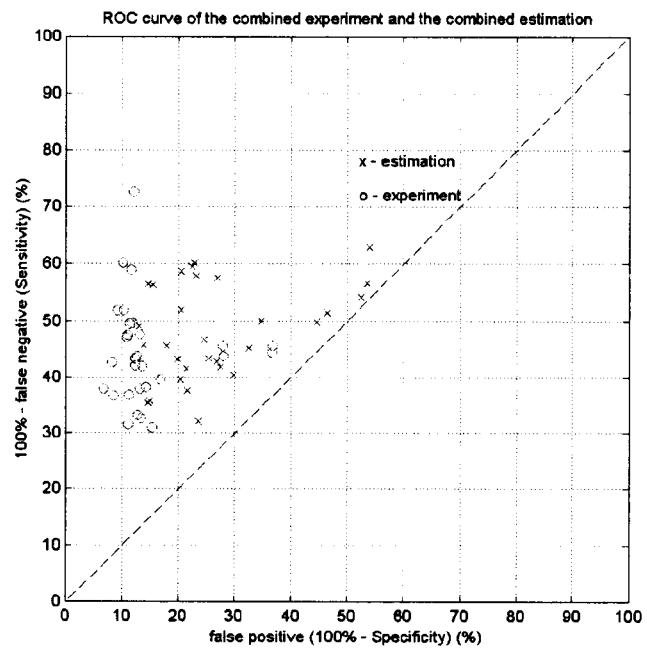

FIG. 14 is the ROC plot for the 30 experiments and the 30 estimations.

Figure 15:
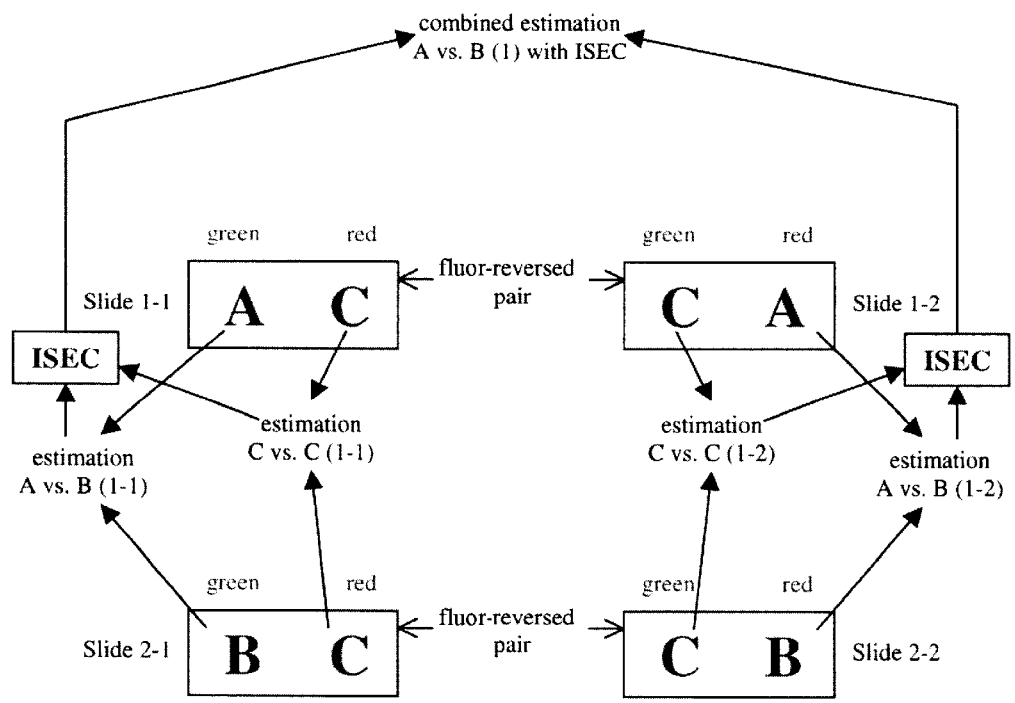
Figure 16:
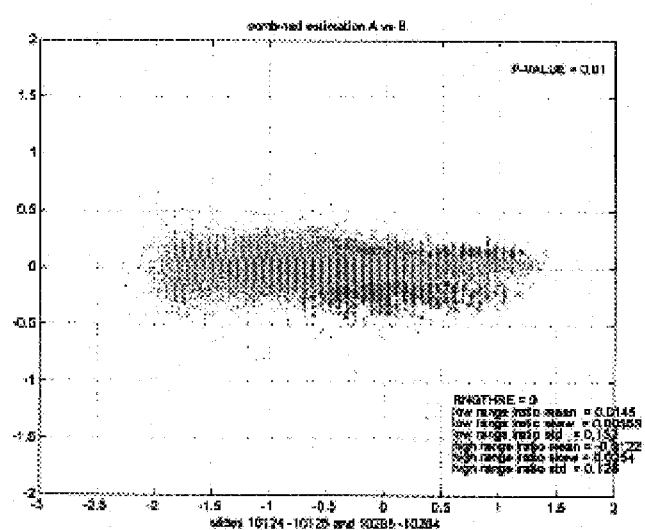

FIG. 15 shows the combination of the estimation A vs. B and the estimation of C vs. C, and the inter-slide error correction (ISEC) process FIG. 16 is a log-ratio plot of an estimation of same-type (ST, or same vs. same), where condition A and condition B are the same.

Figure 17:
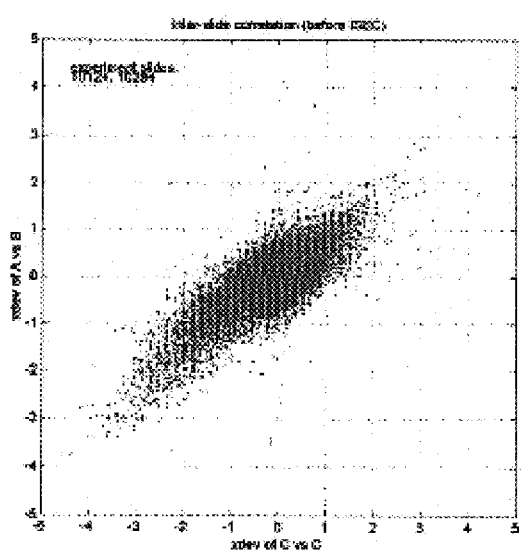

FIG. 17 is a plot of parameter xdev, which is log ratio normalized by its error bar, of an estimation A vs. B(1-1), of which the log-ratio plot is shown in FIG. 16, against the xdev of the ST virtual experiment C vs. C(1-1) from the same pair of slides, Slide 1-1 and Slide 2-1 in FIG. 15.

Figure 18:
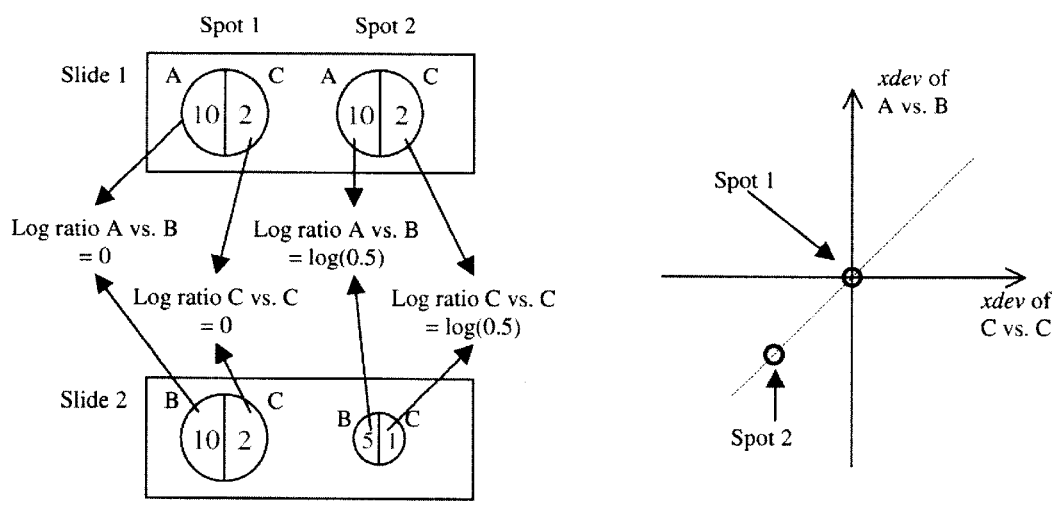

FIG. 18 shows an example of an inter-slide ratio bias.

Figure 19:
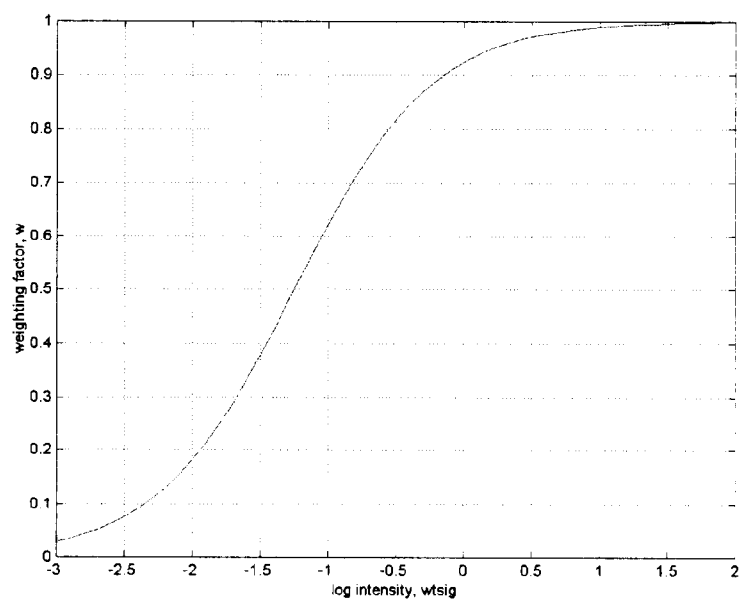

FIG. 19 is a plot of the weighting function.

Figure 20:
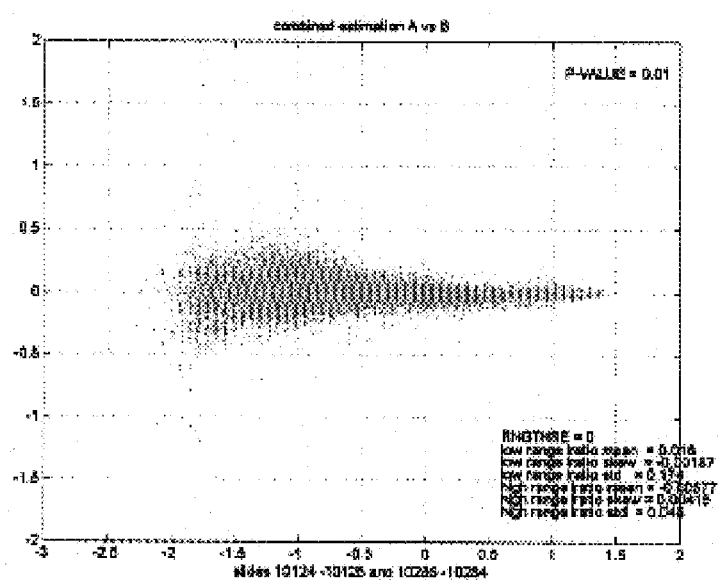

FIG. 20 shows the same data as shown in FIG. 16, except with the error-corrected plots.

Figure 21:
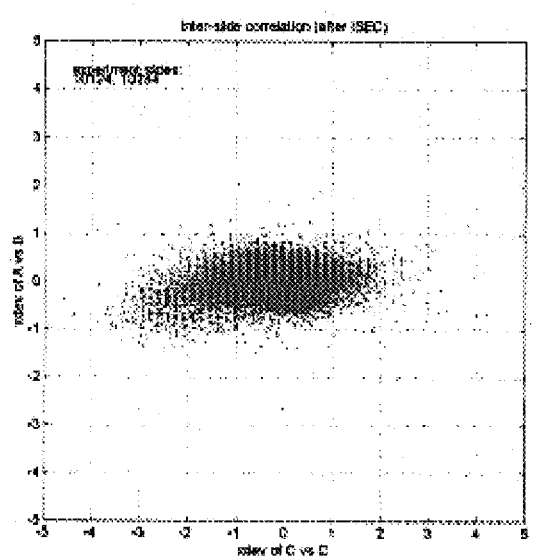

FIG. 21 shows the same data as shown in FIG. 17, except with the error-corrected plots.

Figure 22:
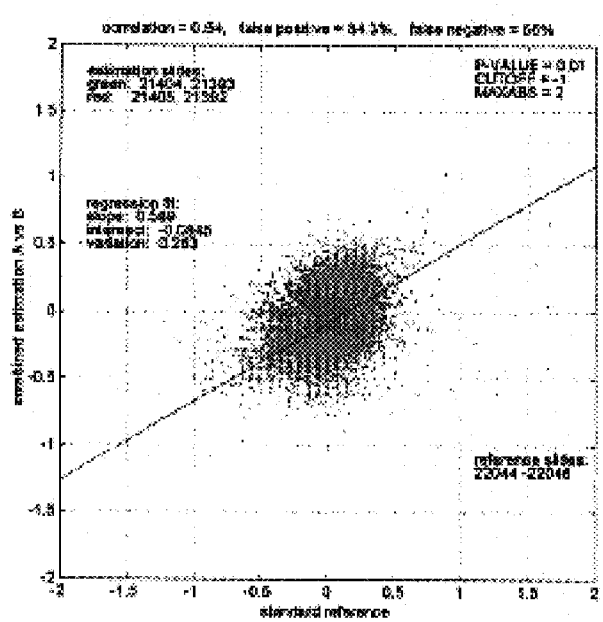

FIG. 22 is a correlation plot without ISEC, between the estimation A vs. B and the real experiment (reference) A vs. B.

Figure 23:
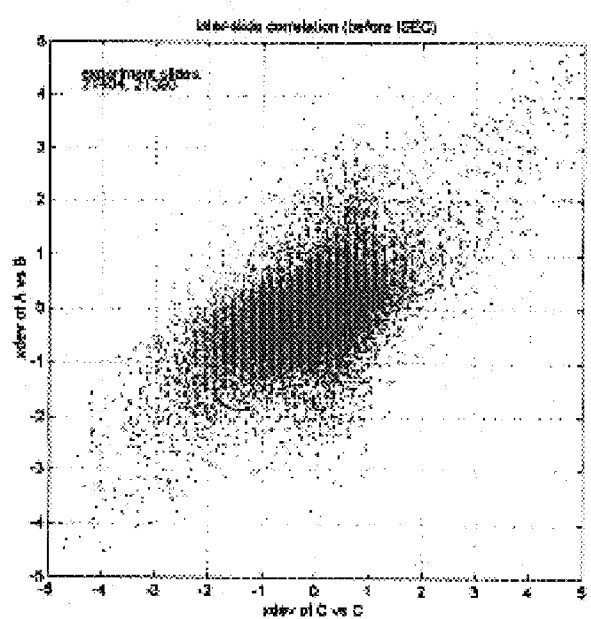

FIG. 23 shows the inter-slide correlation before ISEC.

Figure 24:
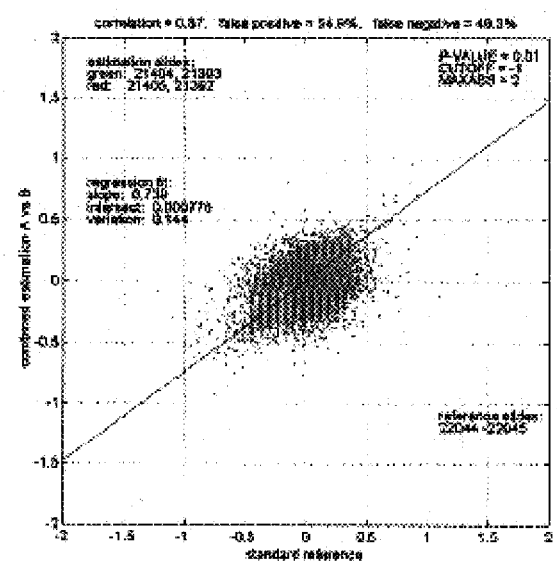

FIG. 24 shows the improvement in correlation plot with ISEC.

Figure 25:
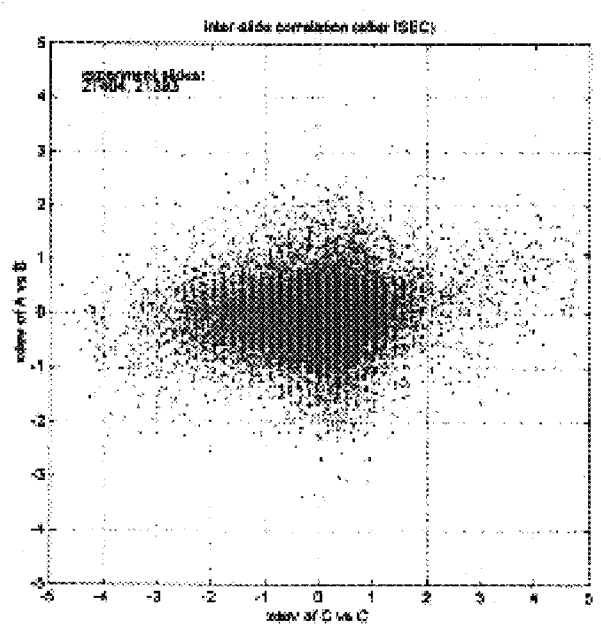

FIG. 25 is the reduced inter-slide correlation after ISEC.

Figure 26:
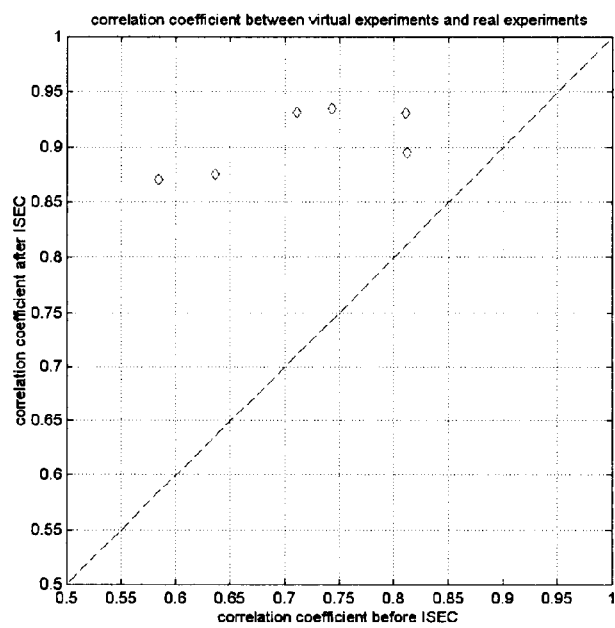
Figure 27:
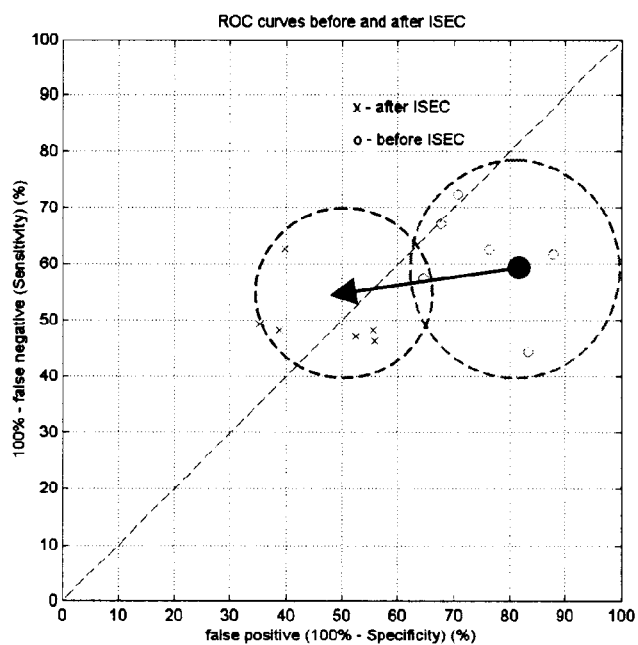

FIG. 26 shows correlation coefficients between the estimation and the experiment for all six sets of data FIG. 27 shows the change in ROC curve after ISEC.

Figure 28:
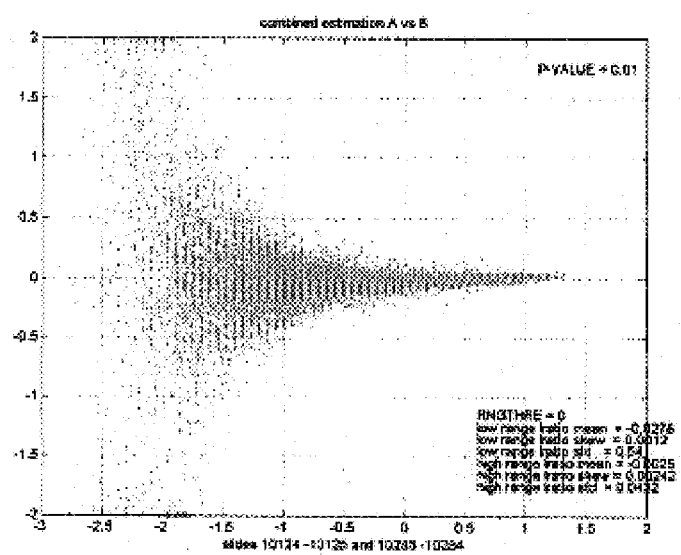

FIG. 28 shows an estimated ST log-ratio plot.

5. DETAILED DESCRIPTION OF THE INVENTION

The present invention provides methods for generating differential profiles by combining data obtained in separate experimental reactions. More specifically, the invention provides methods for generating a differential profile under condition A vs. condition B, designated as A vs. B, from data set A and data set B, which are obtained in separate experimental measurements. In some embodiments, the methods of the invention are used for generating a differential expression profile A vs. B from measured expression profiles A vs. C and B vs. D. The conditions C and D can be the same or different. In a preferred embodiment, when conditions C and D are the same, the invention provides methods for removal or reduction of systematic measurement errors or biases between different experimental reactions, i.e., cross-experiment errors or biases. In other embodiments, the methods of the invention are used for generating a differential profile A vs. B from data obtained in single-channel measurements A and B. The invention also relates to methods for determination of systematic measurement errors between separately performed measurements. In a preferred embodiment, when conditions C and D are the same, the invention provides methods for estimating the cross-experiment errors using expression data measured in samples having been subject to the common condition, i.e., condition C. As an example, and not intended to be limiting, the invention provides methods for generating differential expression profiles by combining data obtained in separate microarray measurements.

As used herein, a differential profile refers to a collection of changes of measurements of cellular constituents, e.g., changes in expression levels of nucleic acid species or changes in abundances of proteins species, in cell samples under different conditions, e.g., under the perturbations of different drugs, under different environmental conditions, and so on. The measurements of cellular constituents, e.g., measured expression levels of nucleic acid species, in a cell sample having been subject to a particular condition, e.g., conditions A, B, or C, are represented as sets of data $\{A(i)\}$, $\{B(i)\}$, and $\{C(i)\}$, respectively, in which i=1, 2, ..., N, and N is the number of measurements of cellular constituents, equivalently, the number of probes used to carry out the measurement. In this disclosure, for convenience, such data sets are often referred to as A, B, or C. The changes in measurements of cellular constituents, e.g., expression levels, can be characterized by any convenient metric, e.g., arithmetic difference, ratio, log(ratio), etc. The mathematical operation log can be any logarithm operations. Preferably, it is the natural log or log10. As used herein, a differential profile A vs. B is defined as a profile representing changes of cellular constituents, e.g., expression levels of nucleic acid species or abundances of proteins species, from A to B, e.g., B–A, when arithmetic difference is used, or B/A, when ratio is used, where the difference or ratio is calculated for each species. Differential profiles resulted from mathematical operations, e.g., arithmetic difference, ratio, log(ratio), etc., on the measured data sets, e.g., A, B, or C, are often referred to by short-hand symbols, e.g., A–B, A/B, or log(A/B). It will be understood by one skill in the art that when such short-hand symbols are used, they refer to data sets representing the differential profiles that contain data points resulted from the respective mathematical operation. For example, differential profile A-B refers to a differential profile comprising data set $\{A(i)-B(i)\}$, whereas differential profile log(B/A) refers to a differential profile comprising data set $\{\log[B(i)/A(i)]\}$. Thus, for example, a differential profile A vs. B can comprise a collection of ratios of expression levels $\{B(i)/A(i)\}$, or log(ratio)'s, i.e., $\{\log[B(i)/A(i)]\}$, and so on. It will be apparent to one skill in the art that a differential profile can be a response profile as described in Section 5.1.2, infra.

In this disclosure, a "same-type" or "ST" differential profile is often referred to. As used herein, a same-type differential profile refers to a differential profile for which the two conditions are the same, e.g., C vs. C. In a preferred embodiment, a same-type differential profile contains data measured from a biological sample in a base-line state. As used herein, a "baseline state" refers to a state of a biological sample that is a reference or control state.

As used herein, a "single-channel measurement" refers broadly to any measurements of cellular constituents made on a sample having been subject to a given condition in a single experimental reaction, whereas a "two-channel measurement" refers to any measurements of cellular constituents made distinguishably and concurrently on two different samples in the same experimental reaction. By same experimental reaction, it is meant in the same reaction mixture, i.e., by contacting with the same reagents in the same composition at the same time (e.g., using the same microarray for nucleic acid hybridization to measure mRNA, cDNA or amplified RNA; or the same antibody array to measure protein levels). Data generated in a single-channel measurement of a sample subject to condition A are often represented as A, whereas data generated in a two-channel measurement of two samples having been subject to conditions A and B, respectively, are often represented as A vs. B. For example, measurement of the expression level of a gene in a cell sample having been subject to an environmental perturbation A obtained in a single color microarray experiment is a single-channel measurement A. On the other hand, measurement of the expression levels of the genes in two cell samples, one having been subject condition A and one having been subject to condition C, obtained in a single two-color fluorescence experiment is a two-channel measurement A vs. C. In some embodiments, a two-channel measurement such as A vs. C can be broken into two separate single-channel measurements A and C. In this invention, a pair of two-channel measurements comprising measurements of samples having been subject to a common condition in one of the two channels are often of interest. In such cases, data associated with the common condition are further identified by their association with the other condition in each two-channel measurement, e.g., $C_A$ identifying data set measured using a sample having been subject to condition C in a two-channel measurement A vs. $C_A$ and $C_B$ identifying data set measured on a sample having been subject to condition C in a two-channel measurement B vs. $C_B$. Any types of single-channel and/or two-channel measurements known in the art can be used in the invention. Preferably, when single-channel measurements are used for generation of a differential profile, the two single-channel measurements are of the same type, e.g., both fluorescence measurements. Expression measurements made distinguishably and concurrently on more than two different samples, e.g., N-color fluorescence experiments, where N is greater than two, can also be used in generation of differential expression profiles by the methods of the present invention.

In this disclosure, methods for generating differential expression profiles of different conditions are described. However, it will be apparent to one skill in the art that the methods are also useful for comparing measured expression profiles of samples having been subject to different conditions. Furthermore, although the methods of the present invention are described for microarray-based expression measurements, it will be apparent to one skilled in the art that the methods of the present invention can also be adapted for generating response profiles of other types of cellular constituents.

5.1. Biological State and Expression Profile

The state of a cell or other biological sample is represented by cellular constituents (any measurable biological variables) as defined in Section 5.1.1, infra. Those cellular constituents vary in response to perturbations, or under different conditions.

5.1.1 Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample), or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes. The other preferred embodiment of the invention employs DNA arrays for measuring expression levels of a large number of exons in the genome of an organism.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S.

$$S = [S_1, \ldots S_i, \ldots S_k] \qquad (1)$$

Where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2 Biological Responses and Expression Profiles

The responses of a biological sample to a perturbation, i.e., under a condition, such as the application of a drug, can be measured by observing the changes in the biological state of the biological sample. A response profile is a collection of changes of cellular constituents. In the present invention, the response profile of a biological sample (e.g., a cell or cell culture) to the perturbation m is defined as the vector $v^{(m)}$:

$$v^{(m)} = [v_1^{(m)}, \ldots v_i^{(m)}, \ldots v_k^{(m)}] \qquad (2)$$

Where $v_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes. In another preferred embodiment of the invention, the biological response to the application of a drug, a drug candidate or any other perturbation, is measured by the induced change in the expression levels of a plurality of exons in at least 2 genes, preferably more than 10 genes, more preferably more than 100 genes and most preferably more than 1,000 genes.

In some embodiments of the invention, the response is simply the difference between biological variables before and after perturbation. In some preferred embodiments, the response is defined as the ratio of cellular constituents before and after a perturbation is applied.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, Detection, Estimation, and Modulation Theory Vol. I, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1+(u/u_0)^n} \quad (3)$$

The adjustable parameters are selected independently for each cellular constituent of the perturbation response. Preferably, the adjustable parameters are selected for each cellular constituent so that the sum of the squares of the differences between the model function (e.g., the Hill function, Equation 3) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, U.S. Provisional Application Serial No. 60/084,742, filed on May 8, 1998, which is incorporated herein by reference for all purposes.

Figure 1:
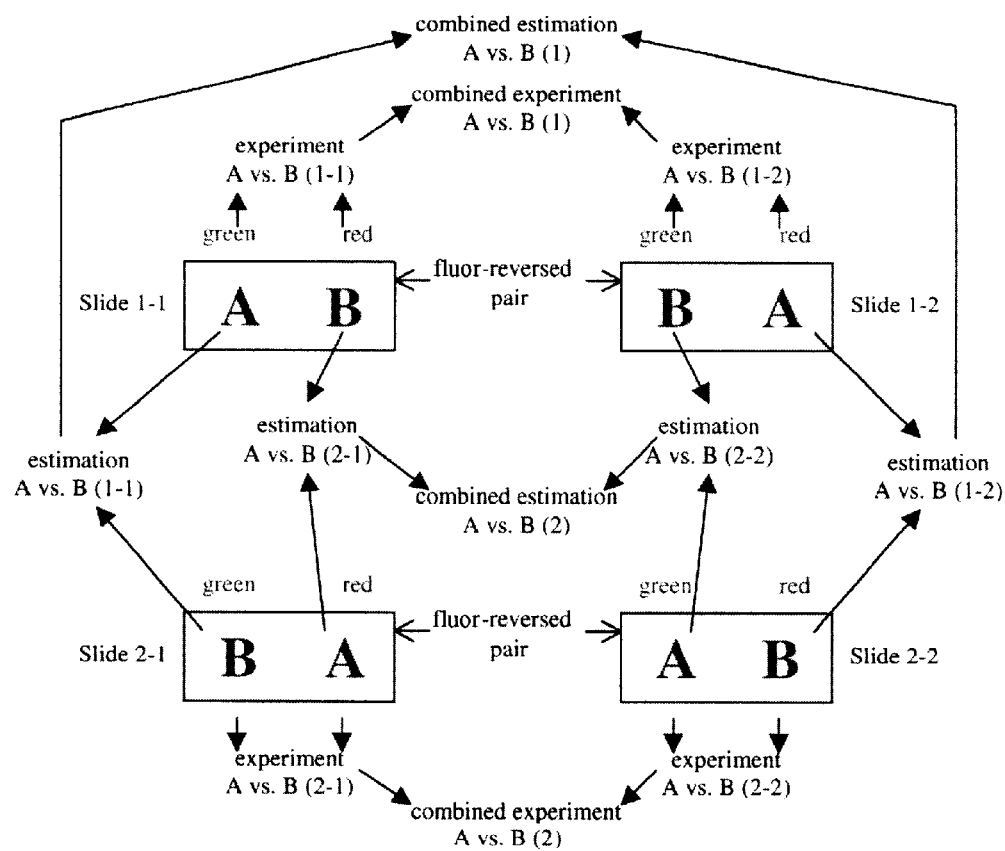
FIG. 1 illustrates the data combination processes in current real experiment and in the virtual experiment (estimation).

5.2. Method of Generating Differential Profiles without Cross-Experiment Error Correction The invention provides methods for generating differential profiles using data from two separate single channel measurements, e.g., measurements from two microarray slides. In one embodiment, an expression profile A vs. B is generated by combining data from two single-channel measured data A and B. In another embodiment, an expression profile A vs. B is generated by combining single-channel data A and B picked up from the separately measured two-channel data A vs. C and B vs. D. In still another embodiment, an expression profile A vs. B is generated by combining single-channel data A and B picked up from two separately measured N-channel data, one containing A and one containing B. In preferred embodiments, data A and B are from channels of the same color in two different slides. Measurement errors in the two channels are removed by removing the additive noise in both channels. When A and B are measured in channels of different colors, color bias is also removed. FIG. 1 illustrates an embodiment of the data combination process. In the illustrated embodiment, single-channel data of the same color from two slides are used to form one estimation of A vs. B(1-1). Another estimation (1-2) comes from their fluor-reversed pairs. These two estimations becomes one combined estimation of A vs. B(1). FIG. 1 also illustrates as a comparison the data combination process in an experiment. In an experiment, each slide generates one result of the ratio of A vs. B. Results from two fluor-reversed slides are combined to form one combined experimental result A vs. B. Two pairs of slides can give two combined experimental A vs. B results (1) and (2). The methods described in this Section are particularly useful for generating differential profiles when changes of cellular constituents between A and B, e.g., changes in expression levels, are strong up-regulated or down-regulated, i.e., the absolute value of the log(ratio) is greater than 0.5 and the normalized average log intensity is high, e.g. the normalized average log intensity is greater than −0.5.

5.2.1. Error Modeling and Error Removal

Typically, the experimental data are very noisy, due to the inherent stochastic nature of the gene expression as well as noises from various external sources. The many sources of error that underlie the experiments fall into two categories—additive and multiplicative. The intensity-independent additive error term includes errors resulted from, e.g., background fluctuation, or spot-to-spot variations in signal intensity among negative control spots, etc., and the intensity-dependent multiplicative term, which is assumed to be directly proportional to the signal intensity, includes errors resulted from, e.g., the scatter observed for ratios that should be unity. When the signal level is high, the multiplicative noise exceeds the level of the additive noise and becomes the dominating factor. An error model correcting for these errors offers a reliable way of identifying those genes that have intensity changes after treatments. For example, for a given confidence level, the error model separates those significant expression changes (signatures) out of the noise.

In one embodiment of the invention, the two error terms are described as follows. For convenience, the description refers to the two data sets, e.g., A and B, as from the "red" channel or the "green" channel, respectively. As will be apparent to one of skill in the art, this is only for the purpose of distinguishing the two data sets. The method is applicable to data sets measured with any other colors. The low-level additive error term is described by a mean and a variance for each of the two fluorescence channels as:

Mean:
  rbkg for the additive background in the red channel;
  gbkg for the additive background in the green channel; and
Variance:
  sigma_$r^2$ for the additive noise in the red channel;
  sigma_$g^2$ for the additive noise in the green channel.

The multiplicative error term is characterized by a multiplicative ratio factor f.

The intensity difference (or ratio) of the red channel and the green channel is normalized by its variance according to Eq. 4, so that a given confidence level (p-value) can be used to measure the distribution of the difference, which has a mean of zero, $$xdev = (r-g)/[sigma\_r^2 + sigma\_g^2 f^2 *(r^2+g^2)]^{1/2} \quad (4)$$

where
  xdev the normalized intensity difference between red and green channels;
  r the intensity of the red channel;
  g the intensity of the green channel;
  f the fractional error ratio between the mutiplicative noise and the signal intensity.

In the methods of the invention, statistical estimation of errors from a plurality of data points is used. Thus, N, the total number of measurements of cellular constituents, used for the methods of the invention is preferably at least 100, more preferably at least 1000, even more preferably at least 10,000.

5.2.2. Estimation of Parameters

The parameters rbkg and gbkg are critical for removing the additive background offsets in the two respective channels. If the offsets are not completely removed and balanced, the logarithmic intensity ratio display of the two channels will have a significant bias in the low intensity end, the so called fish tail, shown in FIG. 2. If the last two parameters sigma_$r^2$ and sigma_$g^2$, the additive noise variances, are incorrectly underestimated, more low intensity spots may be wrongly classified as signatures (see FIG. 3).

In one embodiment, the parameters in Eq. 4 are estimated from a set of same vs. same experiments according to methods described below, and the distribution of xdev is N(0,1).

The ratio f, as estimated from same vs. same experiments, is about 20–25%. During an error model development, we can adjust the parameter f until both a low false positive ratio in same-vs.-same experiment (ST experiment) and a high sensitivity in different are achieved near the high average log intensity side. For a given type of microarry and corresponding reading process, the fractional error ratio can be a constant. In one embodiment, f is chosen to be 0.20.

In another embodiment, when signal-to-background ratio is available, the global means and variances are estimated from the derived background data. An additional residual removal process is applied to estimate and reduce any additive unbalance between two signal channels (red and green).

In this embodiment, experimental data containing data for signal to background ratio, SBR, for the two channels are used to estimate the parameters rbkg, gbkg, sigma_$r^2$, and sigma_$g^2$. SBRs are ratios between signal intensity and background level measured for every spot for the two data channels, treated (the r channel), rSBR, and control baseline (the g channel), gSBR. The background noise data can be derived as following:

$$background\_r = r/rSBR, \text{ noise in the red channel}; \quad (5a)$$

$$background\_g = g/gSBR, \text{ noise in the green channel}. \quad (5b)$$

To compute global statistic parameters for the entire array, we do not need to know the array pattern (rows by columns). Thus, in one embodiment, the additive background mean and standard deviation are calculated as:

$$rbkg = \frac{1}{N} \sum_{i=1}^{N} background \ldots r(i); \text{ and,} \quad (6a)$$

$$gbkg = \frac{1}{N} \sum_{i=1}^{N} background \ldots g(i); \text{ and,} \quad (6b)$$

$$sigma \ldots r = \sqrt{\frac{1}{n-1} \sum_{i=1}^{N} (background \ldots r(i) - rbkg)^2}; \text{ and,} \quad (7a)$$

$$sigma \ldots g = \sqrt{\frac{1}{n-1} \sum_{i=1}^{N} (background \ldots g(i) - gbkg)^2}. \quad (7b)$$

where i is the spot index and N is the total number of spots in the array. N can be less than the total number of spots. For example, some negative control spots may be used for the background calculation.

Other methods for estimating the parameters can also be used in the present invention.

5.2.3. Background Offset Removal

The additive noise mean, i.e., the offset, is then removed from the signal, r, of the red channel, and g, of the green channel, as:

$$r = r - rbkg; \text{ and,} \quad (8a)$$

$$g = g - gbkg. \quad (8b)$$

Figure 2:
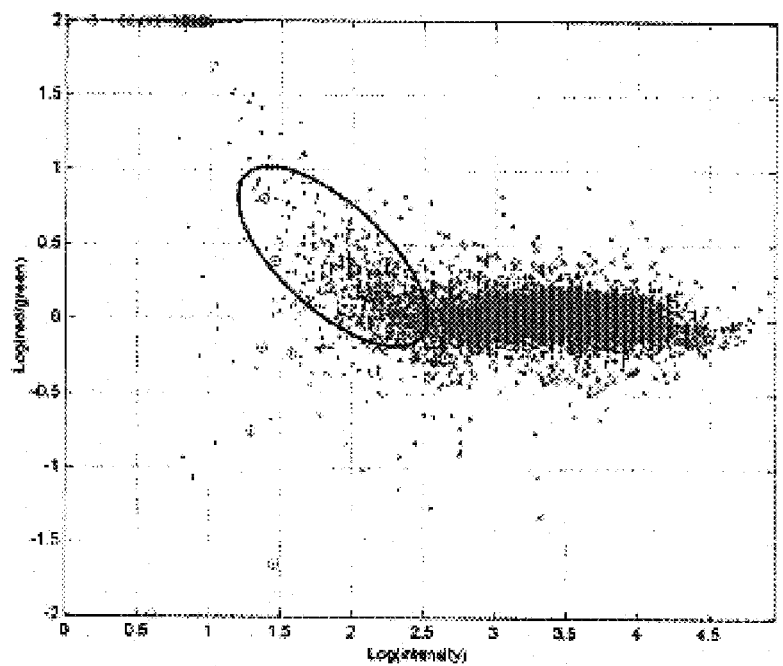
FIG. 2 illustrates skewed fish tail when offsets are not properly removed.

Because the estimation of global background mean may be affected by some systematic background biases, which are not included in the estimation, the background levels of the two channels may still not be balanced even after rbkg and gbkg are removed (see FIG. 2). Thus, in preferred embodiments of the invention, such residual unbalance between the two channels are further estimated and removed.

Small additive residuals in two channels do not need to be completely removed as long as they are equal, or balanced. In one embodiment, a weighted average method is used to estimate the cross-channel residual unbalance. A Gaussian window is applied to the low end of data to reduce the influence of high signal intensity to the estimation. In one embodiment, the estimation uses only positive data, which is more important than the negative data when displaying the logarithmic ratio of intensities. Eq. 9 gives the computation algorithm:

$$residual \ldots c = \left(\sum_i w(i) * r(i)\right) / \left(\sum_i w(i)\right) - \left(\sum_j w(j) * g(j)\right) / \left(\sum_j w(j)\right),$$

for r(i)>0, and g(i)>0, where the weighing function is $$w(k) = e^{-\left(\frac{x(k)}{spread\_c}\right)^2}, x(k) = r(i) \text{ or } x(k) = g(j). \quad (9)$$

In Eq. 9, the parameter spread_c defines the width of the weighing window. A fixed window size is not proper because it may get too much signal or too little background noise into the residual estimation. The approach used in this algorithm finds a proper window width for each specific signal distribution. The window width is adaptive to the distribution width. When r or g intensities spread widely, a large window width will be used in the residual estimation. The concept is shown in FIG. 4, where the low intensity level marks, r_low and g_low, are found for a given percentage spread margin, SM %, e.g., SM % is set to 7% for data obtained from cDNA microarry. FIG. 4 is a conceptual plot of the r intensity distribution after background subtraction defined in Eq. 8a and Eq. 8b. Although the background offset level has been removed, the additive background noise fluctuation still remains, which is conceptually shown as a small bump in the distribution around zero intensity. Parameter SM % is experimentally defined to achieve the best balance of the "fish tail" in the left side of signature plots in FIG. 2. If SM % is too small or too large, the "fish tail" will not be properly balanced as the correct example shown in FIG. 3. Shown in FIG. 4, for a given r intensity distribution (r signal plus noise) and a given SM %, low_r is the intensity level that makes the area between zero and the level under the distribution curve equal to SM % times the area under the curve at left side of the zero intensity. The weighting window width is $$spreadc = \max(r\_low, g\_low) \quad (10)$$

After the cross-channel residual unbalance, residual_c, is found, it is removed from one of the two channels to make them balanced. In one embodiment, the rule to define from which channel the unbalance is removed is to make the data distribution in the channel go lower as described in Equation 8:

$$r = r - residual\_c, \text{ if } residual\_c > 0; \text{ or,}$$

$$g = g + residual\_c, \text{ if } residual\_c <= 0. \quad (11)$$

In preferred embodiments, the procedure for cross-channel residual unbalance removal can be done once. In another embodiment, the procedure can be repeated several times, such as ten times, to further reduce any remaining residuals.

5.2.4. Gain Bias Removal

As described, supra, the two-color fluorescent hybridization process introduces bias into the profile analysis because each species of mRNA that is labeled with fluorophore has a bias in its measured color ratio due to interaction of the fluorescent labeling molecule (fluorophore) with either the reverse transcription of the mRNA or with the hybridization efficiency or both. There is also gain bias caused by the red and green intensity difference in the laser scanner. When the two single-channel data are measured with different labeling colors, e.g., red and green, there may be a constant up or down shift in the generated differential profile, e.g., the logarithmic intensity ratio profile, due to this the fluor or gain bias. Thus, in some embodiments of the invention, e.g., when the two single-channel data are measured with different labeling colors, the gain bias is determined and removed (methods for removing fluor bias is described in Section 5.3.3., infra). In one embodiment, the gain bias is determined by determining the mean intensity of total data in each channel. If the two means from the two channels are different, i.e., there is a gain bias, the data are scaled to one of them, based on the ratio between the means of the two channels. In one embodiment, the red channel is scaled by multiplying the ratio to the red channel data r and sigma__r. In another embodiment, both the red and the green channels are scaled to the averaged value of the mean of the green channel and the mean of the red channel.

5.2.5. Distribution Normalization and Signature Identification

After the additive bias and the color bias are removed, Eq. 4 is used to normalize the distribution of the intensity difference between the two channels. An exemplary normalized distribution of xdev is illustrated in FIG. 5.

For a normal distribution and a given confidence level, the p-value, we can find those data samples outside the confidence level. For example, for p-value is equal to 5%, data samples of X above +1.96 or below −1.96 will be flagged as signatures (see FIG. 5). These signature samples, or spots, are marked by a "x" signs in the logarithmic intensity ratio plot in FIG. 6.

5.2.6. An Embodiment when Direct Background Measurement is not Available

In another embodiment, when direct background measurement or signal-to-background ratio is not available, the low level background statistics are estimated from the signal data. This method is useful when the measurement data contain no data field related to the background noise, and only the signal intensity data is available.

In this embodiment, because the additive noise mean is not known, only the cross-channel residual, residual__c is removed. The procedure is the same as described, supra. The value of SM % is set to an appropriate value.

Variances of the additive background noise, sigma__r$^2$ and sigma__g$^2$ are difficult to estimate. To make a reliable error model in this case, considering the low intensity data is less significant for the analysis of the experiment result, the low level signal spread is used as an approximation of the variance of the background noise. The estimation process is similar to the one described in FIG. 4. By the parameter SM % to 7% and find the low level spread widths, r__low and g__low, in the two channels. Then the standard deviations of the red and the green channels is determined as following:

$$sigma\_r = r\_low; \text{ and} \quad (12a)$$

$$sigma\_g = g\_low. \quad (12b)$$

After sigma__r and sigma__g are estimated, all other processes are the same as those described in Sections 5.2.1 to 5.2.5.

In an optional step, the color bias is removed using the method described in Section 5.2.4.

An example of this embodiment is shown in Example 6.1.

5.3. Method of Generating Differential Profiles with Cross-Experiment Error Correction The invention provides methods for generating a differential profile A vs. B from measured data in A vs. $C_A$ and B vs. $C_B$ measured in two separate experimental reactions. The inventor has discover that the systematic measurement error or bias between the two different experiments, i.e., cross-experiment errors or biases, can be estimated and removed using the data measured with the samples having been subject to the common condition, e.g., condition C. For example, the systematic measurement error between two different two-channel measurements using microarrays, also termed "inter-microarray" or "inter-slide" error, can be estimated and removed using data measured with samples having been subject to the same condition. More specifically, a same-type (ST) differential profile C vs. C is formed using the two sets of separately measured data of sample having been subject to condition C. This ST profile suffers the same inter-slide bias or error as the desired differential profile A vs. B. Thus inter-slide bias or error can be corrected by making use of this ST profile. FIG. 15 shows the inter-slide error correction (ISEC) process. In the methods of the invention, inter-slide error is estimated statistically by calculating a C vs. C from a plurality of data points, e.g., array spots. Thus, the total number of data points N for each data set used in the methods of the invention is preferably at least 100, more preferably at least 1000, even more preferably at least 10,000. Preferably, the methods are used to generate differential profile A vs. B when both $C_A$ and $C_B$ are labeled with the same fluorophore. However, the methods can also be used to generate differential profile A vs. B when $C_A$ and $C_B$ are labeled with different fluorophores. In such embodiments, it is preferable that the fluorophore bias between $C_A$ and $C_B$ are removed before used in generating the ST profile $C_A$ vs. $C_B$. More preferably, the methods are used to generate differential profile A vs. B when A and B are labeled with a first fluorophore and $C_A$ and $C_B$ are labeled with a second fluorophore which is different from the first fluorophore.

5.3.1. Cross-Experiment Correlation

Theoretically, log ratio of a ST experiment should be independent from log ratios of other experiments, regardless the other experiments being ST or not. However, this will not be true when there is systematic inter-slide bias. This can be demonstrated by generating an ST profile from two single-channel measurements of the same condition, e.g., C vs. C using the methods described in Section 5.2. FIG. 16 shows the log-ratio plot of such a generated differential profile C vs. C(1-1). False up- and down-regulations are clearly observable. FIG. 17 shows a plot of parameter xdev (see Equation 1) of an ST profile against the xdev of the corresponding ST profile C vs. C(1-1) measured with the same pair of slides, Slide 1-1 and Slide 2-1. The first ST profile is generated by setting both A and B to be the same as C in FIG. 15. A strong positive correlation between these two profiles are clearly shown in FIG. 17. This correlation is caused by the inter-slide bias. An example of an inter-slide ratio bias is explained in FIG. 18.

Any inter-slide error that systematically causes ratio estimation of A vs. B bias in one direction will product similar bias in the ratio estimation of C vs. C in the same direction, resulted in a positive correlation. An inter-slide error correction method becomes necessary to reduce the bias in the ratio measurement of A vs. B.

5.3.2. The ISEC Algorithm

In one embodiment, the inter-slide bias is removed by subtracting the ST log ratio $C_A$ vs. $C_B$ from the log ratio A vs. B. The subtraction is carried out as described by Eq. 13, which is an objective function, i.e., a log-ratio-error normalized log-ratio difference weighted by a factor w, for the inter-slide error minimization process.

$$\chi^2 = \frac{\sum_{i=1}^{N} \frac{(lratio\ (i) - \alpha \cdot stlratio\ (i))^2}{\sigma_{lratio}^2(i) + \sigma_{stlratio}^2(i)} \cdot w(i)}{\sum_{i=1}^{N} w(i)} \quad (13)$$

where lratio is the log ratio of A vs. B, stlratio is the log ratio of ST C vs. C, $\delta_{lratio}$ and $\delta_{stlratio}$ number of spots in the slide, and $\alpha$ is the de-correlation factor. N can be smaller than the total number of spots in the array. For example, control spots, gridline spots, or spots failed in quality control (QC) inspection may be excluded from Eq. 13. The goal is to find the optimal $\alpha$ that produces the minimum $\chi^2$. By letting $$\frac{\partial \chi^2}{\partial \alpha} = 0, \quad (14)$$

the optimal $\alpha$ can be found as, $$\alpha = \frac{\sum_{i=1}^{N} \frac{lratio(i) \cdot stlratio(i) \cdot w(i)}{\sigma_{lratio}^2(i) + \sigma_{stlratio}^2(i)}}{\sum_{i=1}^{N} \frac{stlratio(i)^2 \cdot w(i)}{\sigma_{lratio}^2(i) + \sigma_{stlratio}^2(i)}}. \quad (15)$$

The weighting factor w is related to the log intensity of C vs. C, stsig. When the log intensity is low, the log ratio of C vs. C, stlratio, becomes inaccurate. In this case, the benefit of de-correlation may not justify the extra error, $\delta_{stlratio}$, added to the newly corrected log ratio of A vs. B. In one embodiment, to reduce the influence of spots with low stsig to the optimization process, a small w(i) to the low stsig(i) spot is assigned. In one embodiment, the weighting factor is defined as $$w(i)=sigmoid((stsig(i)-CENTER)/RANGE), \quad (16)$$

where the function y=sigmoid(x) is defined as $y=1/(1+e^{-x})$. In one embodiment, in which stsig is the log of intensity normalized by the mean intensity so that the mean of the log intensity is near zero, parameter CENTER is set as −1.25, and RANGE is set as 0.5. FIG. 19 is a plot of the weighting function. In general, the selection of parameters CENTER and RANGE depends on the intensity dynamic range above background noise. For typical micro-array intensity data, where the usable dynamic range is about 2.5–3.5 in logarithmic scale, the parameter CENTER can be set to about −1.25 below the mean of the log intensity. The parameter RANGE can be set as 0.5.

The error adjusted log ratio of A vs. B, adjlratio, is computed as $$adjlratio(i)=w(i)\cdot(lratio(i)-\alpha\cdot stlratio(i))+(1-w(i))\cdot lratio(i) \quad (17)$$

When ST log-intensity stsig is high, adjlratio is the difference of the original log ratio lratio and the ST log ratio stlratio. When stsig is low, adjlratio is equal to the original lratio. The new log ratio error, $\delta_{adjlratio}$, is calculated as $$\delta_{adjlratio}^2(i)=w(i)\cdot(\delta_{lratio}^2(i)+\delta_{stlratio}^2(i))+(1-w(i))\cdot\delta_{lratio}^2(i). \quad (18)$$

The new xdev after the inter-slide error correction (ISEC) is $$xdev(i)=adjlratio(i)/\delta_{adjlratio}(i). \quad (19)$$

In another embodiment, the inter-slide bias is removed by subtracting the ST arithmetic difference $C_A$ vs. $C_B$, i.e., $C_B-C_A$, from the arithmetic difference A vs. B. The subtraction, including scaling of the ST profile, is carried out by a method similar to the method for subtraction of log(ratio) as described, supra. In still another embodiment, the inter-slide bias is removed by subtracting the ST ratio $C_A$ vs. $C_B$, i.e., $C_B/C_A$, from the ratio A vs. B. The subtraction, including scaling of the ST profile, is carried out by a method similar to the method for subtraction of log(ratio) as described, supra. It will be apparent to one skilled in the art that the inter-slide bias can also be removed in other types of differential profiles by adapting the method of the present invention to the specific type of differential profiles.

5.3.3. Fluorophore Bias Removal

In preferred embodiments, the generated expression profile A vs. B are further corrected for fluorophore bias if samples under conditions A and B are labeled with different fluorophores. As described, supra, the two-color fluorescent hybridization process introduces bias into the profile analysis because each species of mRNA that is labeled with fluorophore has a bias in its measured color ratio due to interaction of the fluorescent labeling molecule (fluorophore) with either the reverse transcription of the mRNA or with the hybridization efficiency or both. Such a bias is also present in the generated expression profile A vs. B. Thus, in one embodiment, if the fluor-reversed profile B vs. A is also generated, the fluorophore bias can be removed by a method described as follows. See, Stoughton et al., U.S. patent application Ser. No. 09/222,596, filed on Dec. 28, 1998, which is incorporated herein for all purposes.

The fluorophore bias and its removal can be illustrated using the following equations. If we represent the actual molecular abundance of a particular species of mRNA k, representing cellular constituent or gene k in the biological sample of interest, as a(k), the color ratio for probe k, ignoring any source of fluorophore bias may be represented as:

$$\Gamma_{X/Y}=a_A(k)/a_B(k) \quad (20)$$

where
  the subscripts A and B refer to two samples of independently extracted mRNA in which abundances are being compared;

$a_A(k)$ is the abundance of species k in mRNA sample A;

$a_B(k)$ is the abundance of species k in mRNA sample B;

subscripts X and Y represent the two different fluorescent labels used; and $\Gamma_{X,Y}$ is the color ratio that ideally reflects abundance ratio $a_A/a_B$.

However the use of a fluorophore labeled deoxynucleotide triphosphates affects the efficiency by which mRNA is reverse transcribed into cDNA and affects the efficiency to which the flourophore-labeled cDNA hybridizes to the microarray. The precise amount a specific fluorophore affects the transcription or hybridization efficiency is highly dependent upon the precise molecular structure of the fluorophore used. Thus, a direct comparison of $a_A(k)$ to $a_B(k)$, when $a_A(k)$ and $a_B(k)$ are determined using different fluorophores, does not account for these fluorophore-specific affects on transcription and hybridization efficiency. The efficiency of a scanner at determining the abundances $a_A(k)$ and $a_B(k)$ on a microarray is also fluorophore specific. If we represent the combined efficiencies of particular fluorophore in extraction, labeling, reverse transcription, hybridization, and optical scanning as E, a more realistic representation of the color ratio presented in Equation 1 is:

$$\Gamma_{X/Y} = a_A(k) E_X(k) / a_B(k) E_Y(k) \quad (21)$$

where $\Gamma_{X/Y}$ is color ratio;

the subscripts A and B are as defined for Eq. 20;

$a_A(k)$ and $a_B(k)$ are as defined for Eq. 20;

subscripts X and Y are two fluorescent labels;

$E_X(k)$ is the efficiency of flourescent label X; and $E_Y(k)$ is the efficiency of flourescent label Y.

In Eq. 21, sample A has been analyzed using fluorophore X whereas sample B has been analyzed using fluorophore Y. Now the color ratio F is related to the desired abundance ratio $a_A/a_B$ but includes a factor due to the fluorophore specific efficiency biases. If a second hybridization experiment is performed, wherein sample A is now analyzed with fluorophore Y and sample B is analyzed using fluorophore X, the color ratio in the second hybridization experiment may be represented as:

$$\Gamma_{X/Y}^{(rev)} = a_B(k) E_X(k) / a_A(k) E_Y(k) \quad (22)$$

where $\Gamma_{X/Y}^{(rev)}$ is color ratio in the reverse experiment; and $a_B(k)$, $a_A(k)$, $E_X(k)$, and $E_Y(k)$ are as described for Eq. 21

Performing hybridization experiments in pairs, with the label assignment reversed in one member of the pair, allows for creation of a combined average measurement in which the fluorophore specific bias is sharply reduced. For example a pair of two-flourophore hybridization experiments may be performed. The first two-fluorophore experiment would be performed in accordance with Eq. 21 and the second two-fluorophore hybridization experiments would be performed according to Eq. 22. If the log of the ratio of the two experiments is taken, the combined experiment can be expressed as:

$$(1/2)(log(\Gamma_{X/Y}) - log(\Gamma_{X/Y}^{(rev)})) = log(a_A(k)/a_B(k)) + (log(E_X(k)/E_Y(k)) - log(E_X(k)/E_Y(k))) = log(a_A(k)/a_B(k)) \quad (23)$$

which is the desired log abundance ratio. Cancellation of the bias terms $log(E_X(k)/E_Y(k))$ and $log(E_X(k)/E_Y(k))$ relies on constancy of the biases between the first and second hybridization experiments in each fluorophore-reversed pair. Eq. 23 can be written equivalently using ratios as found in Eqs. 20–22 instead of differences of log ratios. However, changes in constituent levels are most appropriately expressed as the logarithm of the ratio of abundance in the pair of conditions forming the differential measurement. This is because fold changes are more meaningful than changes in absolute level, biologically.

In another embodiment, when the fluor-reversed profile B vs. A is not available, the fluorophore bias removal can be achieved by viewing A and B as two single-channel data and applying the method described in Section 5.2.

5.3.4. Method of Comparing Expression Data Measured at Different Hybridization Times The invention also provides methods for generating differential expression profile $A(T_1)$ vs. $A(T_2)$ from data measured at different hybridization times $T_1$ and $T_2$, i.e., different lengths of hybridization durations, in two separate measurements, thereby comparing expression data measured at the two hybridization times. Methods described in both Sections 5.2. and 5.3. can be used for this purpose. In one embodiment, the methods described in Section 5.2, supra, are used to generate a differential expression profile $A(T_1)$ vs. $A(T_2)$ from data sets $A(T_1)$ and $A(T_2)$ measured in single-channel experiments of A at hybridization times $T_1$ and $T_2$. In another embodiment, the methods described in Section 5.3, supra, are used to generate a differential expression profile $A(T_1)$ vs. $A(T_2)$ from $A(T_1)$ vs. $C(T_1)$ and $A(T_2)$ vs. $C(T_2)$ measured in two separate two-channel experiments of A vs. C at hybridization times $T_1$ and $T_2$. Such methods are useful when changes in hybridization levels in time are to be determined, e.g., in methods in which hybridization kinetics is used for distinguishing hybridization specificity at different hybridization time (see U.S. Provisional Patent Application Serial No. To be assigned, Attorney Docket No. 9301-097-888, filed on Apr. 26, 2001, which is incorporated by reference herein in its entirety). For this purpose, the first hybridization level can be measured at between 1 to 10 hours, whereas the second hybridization time can be measured at about 2, 4, 6, 10, 12, 16, 18, 48 or 72 times as long as the first hybridization time. The invention thus provides a method for correcting any systematic errors that may arise between measurements carried out at different hybridization times. It will be apparent to one skilled in the art that the methods as described in this Section can be applied to compare expression data measured at more than two different hybridization times.

5.3.5. Method of Comparing the Quality of Microarrays

One embodiment of the invention provides a method for controlling the quality of microarray slide production process.

Refer back to FIG. 15, which illustrates a typical ISEC process. As a simpler variation, only two slides, slide 1-1 and slide 2-1, are needed here. For controlling production quality application, their fluor-reversed pairs, slide 1-2 and slide 2-2, are not necessary.

As a result, one good quality slide needs to be selected to serve as a standard. A second microarray slide is then randomly selected from a batch of production slide. Unlike FIG. 15, where slide 1-1 is experiment A vs. C and slide 2-1 is experiment B vs. C, one may easily construct two identical same-type virtual experiments C vs. C for both slides.

As explained earlier, log ratio of an ST experiment should be independent from log ratios of other experiments. This is especially the case given that the other experiment is also an ST experiment. Therefore, in a plot similar to FIG. 16, where the log ratio of one virtual experiment (C vs. C with color label 1) against log ratio of another virtual experiment (C vs. C with color label 2), there should be no correlation. Correlation can be accurately measured quantitatively using coefficient of correlation.

The coefficient of correlation (G, with $-1<=G<=+1$) is a number that indicates both direction and the strength of the linear relationship between the dependent variable and the independent variable. It can be calculated using the following equation:

$$G = \frac{n(\Sigma x_i y_i) - (\Sigma x_i)(\Sigma y_i)}{\sqrt{n(\Sigma x_i^2) - (\Sigma x_i)^2} \cdot \sqrt{n(\Sigma y_i^2) - (\Sigma y_i)^2}} \quad (24)$$

If G is positive, two variables are directly related. If G is negative, the variables are inversely related.

In this case, however, the strength of the relationship is more important. The larger the absolute value of G, the stronger the linear relationship between the two variables. If $G=-1$ or $G=+1$, the regression line will actually include all of the data points. When $G=0$, there is no linear relationship whatsoever between the two variables. In this case, the log ratio of one experiment is entirely independent of the log ratio of another experiment.

Therefore, when microarray slides are produced properly, the coefficient of correlation (G) should be zero or close to zero. When the absolute value G is large (close to 1), it indicates a strong correlation, thus it is a strong indication of defectively manufactured slide.

A quantitative production quality control process can thus be established by first computing a correlation coefficient using the intensity ratio of the first virtual experiment (C vs. C with color label 1) and the intensity ratio of the second virtual experiment (C vs. C with color label 2) by an inter-slide correlation method, and then judging the quality of microarray slides by using a predetermined range of correlation coefficient. For example, the range of acceptable correlation coefficient can be set to be between -0.5 and 0.5.

5.4. Implementation Systems and Methods

The analytical methods of the present invention can preferably be implemented using a computer system, such as the computer system described in this section, according to the following programs and methods. Such a computer system can also preferably store and manipulate a compendium of the present invention which comprises a plurality of perturbation response profiles and which can be used by a computer system in implementing the analytical methods of this invention. Accordingly, such computer systems are also considered part of the present invention.

An exemplary computer system suitable from implementing the analytic methods of this invention is illustrated in FIG. 7. Computer system 701 is illustrated here as comprising internal components and as being linked to external components. The internal components of this computer system include a processor element 702 interconnected with a main memory 703. For example, computer system 701 can be an Intel Pentium®-based processor of 200 MHZ or greater clock rate and with 32 MB or more main memory. In a preferred embodiment, computer system 701 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 704. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 705, which is most typically a monitor and a keyboard together with a graphical input device 706 such as a "mouse." The computer system is also typically linked to a network link 707 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 7. The software components comprise both software components that are standard in the art and components that are special to the present invention. These software components are typically stored on mass storage such as the hard drive 704, but can be stored on other computer readable media as well including, for example, one or more floppy disks, one or more CD-ROMs, one or more DVDs or one or more DATs. Software component 710 represents an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components 711 comprises common languages and functions that are preferably present in the system to assist programs implementing methods specific to the present invention. Languages that can be used to program the analytic 5 methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 712 comprises any analytic methods of the present invention described supra, preferably programmed in a procedural language or symbolic package. For example, software component 712 preferably includes programs that cause the processor to implement steps of accepting a plurality of measured expression profiles and storing the profiles in the memory. For example, the computer system can accept exon expression profiles that are manually entered by a user (e.g., by means of the user interface). More preferably, however, the programs cause the computer system to retrieve measured expression profiles from a database. Such a database can be stored on a mass storage (e.g., a hard drive) or other computer readable medium and loaded into the memory of the computer, or the compendium can be accessed by the computer system by means of the network 707.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

5.5. Methods for Determining Biological State and Biological Response

This invention provides methods for generating differential expression profiles by combining data measured in separate experiments, e.g., separate microarray experiments. The data can be measured from cell samples subject to different conditions, e.g., under different perturbations. The cell sample can be of any organism, e.g., eukaryote, mammal, primate, human, non-human animal such as a dog, cat, horse, cow, mouse, rat, Drosophila, *C. elegans*, etc., plant such as rice, wheat, bean, tobacco, etc., and fungi. The cell sample can be from a diseased or healthy organism, or an organism predisposed to disease. The cell sample can be of a particular tissue type or development stage or subjected to a particular perturbation (stimulus). The measured expression profiles of different cell samples can be combined and compared to generate expression profiles to assess differences between the biological states of such different cell samples. for example, perturbed vs. nonperturbed, e.g., diseased vs. healthy cell samples. This section and its subsections provides some exemplary methods for measuring the expression profiles of cell samples. One of skill in the art would appreciate that this invention is not limited to the following specific methods for measuring the expression profiles and responses of a biological system.

5.5.1. Transcript Assay Using Microarrays

This invention is particularly useful for the determination of the expression state or the transcriptional state of a cell or cell type or any other cell sample by monitoring expression profiles. One aspect of the invention provides polynucleotide probe arrays for simultaneous determination of the expression levels of a plurality of genes and methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundance ratios.

Preferably, measurement of the expression profile is made by hybridization to transcript arrays, which are described in this subsection In a preferred embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest. In another embodiment, the cell sample can be from a patient, e.g., a diseased cell sample, and preferably can be compared to a healthy cell sample.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40–60 bases. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000 probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some other embodiments of the invention, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15–600 bases, preferably between about 20–200 bases, more preferably between about 30–100 bases, and most preferably between about 40–80 bases. The average length of an exon is about 200 bases (see, e.g., Lewin, *Genes V,* Oxford University Press, Oxford, 1994). A probe of length of about 40–80 allows more specific binding of the exon than a probe of shorter length, thereby increasing the specificity of the probe to the target exon. For certain genes, one or more targeted exons may have sequence lengths less than about 40–80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some other embodiments of the invention, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546–567). In contrast, the human genome is estimated to contain approximately 30,000 to 130,000 genes (see Crollius et al., 2000, *Nature Genetics* 25:235–238; Ewing et al., 2000, *Nature Genetics* 25:232–234). Genome sequences for other organisms, including but not limited to Drosophila, *C. elegans,* plants, e.g., rice and Arabidopsis, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467–470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0–72 hours. Appropriate hybridization times for other embodiments will depend on the particular polynucleotide sequences and probes used, and may be determined by those skilled in the art (see, e.g., Sambrook, J. et al, supra).

The method of the invention relies on measurement of hybridization levels at more than one hybridization time. In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.5.2. Preparing Probes for Microarrays

As noted above, the "probe" to which a particular polynucleotide molecule, such an exon, specifically hybridizes according to the invention is a complementary polynucleotide sequence. The probes for exon profiling arrays are selected based on known and predicted exons determined in Section 5.2. Preferably one or more probes are selected for each target exon. Depending on the probe scheme as described in Section 5.4.1., the lengths and number of probes for each exon are chosen accordingly. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40–60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications,* Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.5.3. Attaching Probes to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467–470. This method is especially useful for preparing microarrays of cDNA (See also, DeRisi et al, 1996, *Nature Genetics* 14:457–460; Shalon et al, 1996, *Genome Res.* 6:639–645; and Schena et al., 1995, *Proc. Natl. Acad. Sci. U.S.A.* 93:10539–11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679–1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111–123).

5.5.4. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294–5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. patent application Ser. No. 09/411,074, filed Oct. 4, 1999 by Linsley and Schelter and U.S. Provisional Patent Application Serial No. 60/253,641, filed on Nov. 28, 2000, by Ziman et al.). Both oligo-dT primers (U.S. Pat. Nos. 5,545,522 and 6,132,997) or random primers (U.S. Provisional Patent Application Serial No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluoescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.5.5. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology,* Greene Publishing and Wiley-Interscience, New York. When the cDNA microarrays of Schena et al. are used, typical hybridization conditions are hybridization in 5× SSC plus 0.2% SDS at 65° C. for four hours, followed by washes at 25° C. in low stringency wash buffer (1× SSC plus 0.2% SDS), followed by 10 minutes at 25° C. in higher stringency wash buffer (0.1× SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes,* Elsevier Science Publishers B.V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.5.6. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced by from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467–470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

In other preferred embodiments, single-channel detection methods, e.g., using one-color fluorescence labeling, are used (see U.S. provisional patent application Serial No. 60/227,966, filed on Aug. 25, 2000). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, an exon is called present if the intensity difference between the FS probe and the corresponding RC probe is significant. More preferably, an exon is called present if the FS probe intensity is also significantly above background level. Single-channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Res. 6:639–645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, Genome Res. 6:639–645. Alternatively, the fiber-optic bundle described by Ferguson et al., 1996, Nature Biotech. 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.6. Measurement of Drug Response Data

Drug responses are obtained for use in the instant invention by measuring the exon expression state changed by drug exposure. The biological response described on the exon level can be measured by exon profiling methods described in the previous sections. The measured response data include values representing exon expression level values or exon expression level ratios for various exons in a plurality of genes, which can reflect both DNA expression ratios (in the absence of differences in RNA degradation rates) and alternative RNA splicing ratio.

To measure drug response data, cell are exposed to graded levels of the drug or drug candidate of interest. When the cells are grown in vitro, the compound is usually added to their nutrient medium. The drug is added in a graded amount that depends on the particular characteristics of the drug, but usually will be between about 1 ng/ml and 100 mg/ml. In some cases a drug will be solubilized in a solvent such as DMSO.

The exon expression profiles of cells exposed to the drug and of cells not exposed to the drug are measured according to the methods described in the previous section. Preferably, exon transcript arrays are used to find the genes with altered exon expression profiles due to exposure to the drug.

It is preferable for measurements of drug responses, in the case of two-colored differential hybridization described above, to measure with reversed labeling. Also, it is preferable that the levels of drug exposure used provide sufficient resolution of rapidly changing regions of the drug response, e.g., by using approximately ten levels of drug exposure.

5.7. Methods for Probing Biological States

One aspect of the invention provides methods for the analysis of biological state. The methods of this invention are also useful for the analysis of responses of a cell sample to perturbations designed to probe cellular state. Preferred perturbations are those that cause a change in the amount of alternative splicing that occurs in one or more RNA transcripts. This section and its subsections herein below provide some illustrative methods for probing exon expression states.

Methods for targeted perturbation of cells are increasingly widely known and applied in the art. The following methods are exemplary of those that can be used to produce modifications in the exon expression profile of a cell sample.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general).

5.7.1. Titratable Expression Systems

In mammalian cells, several means of titrating expression of genes are available (Spencer, 1996, Trends Genet. 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci. USA 89:5547–5551; Hoffmann et al., 1997, Nucl. Acids. Res. 25:1078–1079; Hofmann et al., 1996, Proc. Natl. Acad. Sci. USA 83:5185–5190; Paulus et al., 1996, Journal of Virology 70:62–67). Another commonly used controllable promoter system in mammalian cells is the ecdysone-inducible system developed by Evans and colleagues (No et al., 1996, Proc. Nat. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Proc. Nat. Acad. Sci. USA 93:4604–4607; Spencer, 1996, Trends Genet. 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122:4149–4157; Spradling et al., 1995, Proc. Natl. Acad. Sci. USA, 92:10824–10830; Ramirez-Solis et al., 1993, Methods Enzymol. 225:855–878; and Thomas et al., 1987, Cell 51:503–512.

5.7.2. Transfection Systems for Mammalian Cells

Transfection or viral transduction of target genes can introduce controllable perturbations in biological exon expression states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1+/−system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation exon expression state (Anderson et al., 1994, Adv. Immunol. 56:171–178). Inhibitors of this enzyme are of interest as potential immunosuppressive drugs (Hanke, 1996, J. Biol Chem 271:695–701). A specific mutant of the Jurkat T cell line (JCaM1) is available that does not express Ick kinase (Straus et al., 1992, Cell 70:585–593). Therefore, introduction of the Ick gene into JCaM1 by transfection or transduction permits specific perturbation of exon expression states of T cell activation regulated by the Ick kinase. The efficiency of transfection or transduction, and thus the level of perturbation, is dose related. The method is generally useful for providing perturbations of gene expression or protein abundances in cells not normally expressing the genes to be perturbed.

5.7.3. Methods of Modifying RNA Abundances or Activities

Methods of modifying RNA abundances and activities and thus exon abundances currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15: 287–299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et 1 al., 1987, Nucl. Acids Res. 15: 6131–6148), or a chimeric RNA-DNA analog (Inoue et al., 1987, FEBS Lett. 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

In still another embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

Post-transcriptional gene silencing (PTGS) or RNA interference (RNAi) can also be used to modify RNA abundances (Guo et al., 1995, Cell 81:611–620; Fire et al., 1998, Nature 391:806–811). In RNAi, dsRNAs are injected into cells to specifically block expression of its homologous gene. In particular, in RNAi, both the sense strand and the anti-sense strand can inactivate the corresponding gene. It is suggested that the dsRNAs are cut by nuclease into 21–23 nucleotide fragments. These fragments hybridize to the homologous region of their corresponding mRNAs to form double-stranded segments which are degraded by nuclease (Grant, 1999, Cell 96:303–306; Tabara et al., 1999, Cell 99:123–132; Zamore et al., 2000, Cell 101:25–33; Bass, 2000, Cell 101:235–238; Petcherski et al., 2000, Nature 405:364–368). Therefore, in one embodiment, one or more dsRNAs having sequences homologous to the sequences of one or more mRNAs whose abundances are to be modified are transfected into a cell or tissue sample. Any standard method for introducing nucleic acids into cells can be used.

6. EXAMPLES

The following examples are presented by way of illustration of the present invention, and are not intended to limit the present invention in any way.

6.1. Generating Differential Profiles without Inter-Slide Error Correction

This example illustrates the methods of the invention for generating differential profiles without inter-slide error correction.

Sixty (60) microarray slides were used to test the methods for generating differential profiles without inter-slide error correction. These microarray slides were designed for quality control (QC) in the array production process. The two samples that were hybridized to these slides were Jurkat (A) vs. K562 (B). They were hybridized to the 60 slides in thirty (30) fluor-reversed pairs.

FIG. 1 illustrates the data combination schemes used in this example. In the experimental scheme, i.e., generating differential profile (the "experimental profile" labeled with "experiment" in FIG. 1) from a two-channel measurement, data obtained from each slide give one profile, e.g., a ratio profile, A vs. B. Profiles from two fluor-reversed slides were combined to form one combined (i.e., color-corrected) experimental profile A vs. B. Thus, two pairs of slides, e.g., slides 1-1 and 1-2 and slides 2-1 and 2-2 as shown in FIG. 1, give two experimental profiles A vs. B as indicated as A vs. B(1) and (2). In the scheme using the methods of the invention (described in Section 5.2.), single-channel data of the same color from two slides were used to generate one computed profile A vs. B(1-1) (the "computed profile", labeled with "estimation" in FIG. 1). Another computed profile A vs. B(1-2) were generated from their fluor-reversed pairs. These two computed profiles were then combined to form one combined computed profile A vs. B(1). Another combined computed profile A vs. B(2) was similarly generated. Thus, using four QC slides, two computed profiles A vs. B, estimation (1) and (2) as shown in FIG. 1, were generated. Therefore, 60 QC slides (30 fluor-reversed pairs) in this example were used to generate 30 combined experimental profiles A vs. B and 30 combined computed profile A vs. B. These 30 combined experimental profiles and 30 combined computed profile were compared to a standard reference profile so that their merit can be evaluated. The reference profile in this example was a combined profiles generated by averaging 5 experimental profiles, each from a fluor-reversed pairs of good quality QC slides. These 5 pairs were not part of the 30 pairs of slides used in the evaluation. FIG. 8 shows a log-ratio plot of the reference profile. Up- or down-regulated spots are marked by a "x" for P-value 0.01. When computing the P-value, parameter xdev for the 5-pair averaged reference profile was divided by $\sqrt{5}$ so that it is comparable to that for the experimental profiles, each which were generated from a single pair of slides (four channels of data from two slides), or the single-pair computed profiles (four channels of data from four slides).

FIG. 9A shows a log-ratio plot of a combined experimental profile A vs. B. FIG. 9B shows a correlation plot of this combined experimental profile and the reference profile. In FIG. 9B only those spots having a log intensity higher than −1 are shown. Correlation was computed on the set of signature union from both the experiment and the reference. False positive was defined as the ratio (in term of percentage) of the number of spots that are signatures in the experimental profile but not signatures in the reference profile and the total number of signatures in the experimental profile. Similarly, false negative was defined as the ratio (in term of percentage) of number of spots that are not signatures in the experimental profile but signatures in the reference profile and the total number of signatures in the reference profile.

FIG. 10A and FIG. 10B show the results of a combined computed profile. Both ratio plot of the experimental profile and the computed profile are very similar to the reference profile. Signatures in both the experimental profile and the computed profile correlate well with those in the reference profile. But the computed profile has a slightly higher false positive, which was caused by inter-slide bias.

FIG. 11 displays the histograms of the correlation coefficients between the combined experimental profile and the reference profile and the combined computed profile and the reference profile. A null hypothesis was formed by subtracting the correlation coefficient of the combined experimental profile from the correlation coefficient of the combined computed profile. A t-test was performed on the null hypothesis. The resulted p-value was 0.47, indicating that the difference between the correlation coefficients of the combined experimental profile and the combined computed profile was statistically insignificant for these 60 slides.

FIG. 12 displays the histograms of the false positive of the combined experimental profile and combined computed profile. A null hypothesis was formed by subtracting the false positive of the experimental profile from the false positive of the computed profile. A t-test was performed on this null hypothesis. The result p-value was 1.37e-7, which indicates that the false positive rate of the combined experimental profile and the false positive rate of the combined computed profile are statistically significantly different. A further test indicates the false positive rate difference is in a range [+8.6%, +15.8%] with confidence p-value less than 0.05. We can conclude from these two tests that the false positive rate of the computed profile is statistically higher than the false positive rate of the experimental profile for these 60 slides.

FIG. 13 shows the histograms of the false negative of the combined experimental profile and combined computed profile. A null hypothesis was formed by subtracting the false negative of the experimental profile from the false negative of the computed profile. A t-test was performed on this null hypothesis. The result p-value was 0.01, which indicates that the false negative rate of the combined experimental profile and the false negative rate of the combined computed profile are statistically significantly different. A further test indicates the false negative rate difference is in a range [−6.5%, −0.9%] with confidence p-value less than 0.05. We can conclude from these two tests that the false negative rate of the computed profile is statistically lower than the false negative rate of the experimental profile for these 60 slides.

Because the computed profile has a higher false positive but a low false negative, it is impossible to determine which is a more accurate profile by looking at false positive or false negative separately. To combine the information of the false positive and the false negative together for a better evaluation, a ROC (Receiver Operating Characteristic) curve was constructed, which has the false positive (100%-Specificity) as the horizontal axis and the false negative (100%-Sensitivity) as the vertical axis. FIG. 14 shows the ROC plot for the 30 experimental profiles and the 30 computed profiles of this example.

The ROC analysis shows that there is a tradeoff between sensitivity and specificity (any increase in sensitivity will be accompanied by a decrease in specificity). The closer the curve follows the left-hand border and then the top border of the ROC space, the more accurate the test. The closer the curve comes to the 45-degree diagonal of the ROC space, the less accurate the test. The area under the curve is a measure of test accuracy. In FIG. 14, the trend of the ROC curves for the experimental profiles and the experimental profiles were mixed, therefore, the difference in accuracy between the two was not significant for these QC slides.

In summary, for the sixty QC slides, which show strong signatures, the computed profiles are similarly accurate as compared to the experimental profiles.

6.2. Generating Differential Profiles with ISEC

This example illustrates the methods of the invention for generating differential expression profiles with inter-slide error correction.

ISEC method as described in Section 5.3. was applied to the same data as shown in FIG. 16 and FIG. 17. FIG. 20 and FIG. 21 show expression profiles generated by the method.

The false signatures in FIG. 16 are disappeared in FIG. 20. The inter-slide correlation between the ratio of A vs. B and the ratio of C vs. C is significantly reduced as shown in FIG. 21.

To test the improvement by the ISEC algorithm to the accuracy of ratio estimation in computed profiles having weak signatures, the computed profiles generated by method with and without ISEC were compared using six (6) sets of data that have experimental profiles A vs. B as references. FIG. 22 shows for one set of data a correlation plot without ISEC between the computed profile A vs. B and the experimental profile A vs. B. FIG. 23 shows the inter-slide correlation before ISEC were applied to the data. FIG. 24 shows the improvement in correlation plot after application of ISEC to the data. FIG. 25 shows the reduced inter-slide correlation after application of ISEC to the data.

It is clearly shown in FIG. 24 that after ISEC the correlation between the computed profile and the experimental profile was significantly improved (compare to FIG. 22 for computed profile without applying ISEC), whereas the false positive rate was much reduced. After ISEC, as shown in FIG. 25, the inter-slide correlation between the computed ratio A vs. B and the ST ratio C vs. C was greatly reduced.

For all six sets of data, correlation coefficients between the computed profile and the experimental profile were all significantly increased. The result is shown in FIG. 26. The change in ROC curve after ISEC is shown in FIG. 27. The center of the ROC spots after ISEC (marked with "x") moves from below the 45-degree diagonal line to above it. This indicates an increase in the accuracy of the computed profile.

When log-ratios of real experiment data A vs. $C_A$, AClratio, and B vs. $C_B$, Bclratio are available, it is also possible to obtain the log-ratio of the virtual experiment A vs. B, estlratio, by $$estlratio = \log(B/A) \approx \log\left(\frac{C_a/A}{C_b/B}\right). \quad (25)$$
$$= \log(C_a/A) - \log(C_b/B)$$
$$= AClratio - BClratio$$

The log-ratio error, $\delta_{estlratio}$, of the estimated log-ratio is calculated as $$\delta_{estlratio}^2 = \delta_{AClratio}^2 + \delta_{BCwtlratio}^2 \quad (26)$$

The parameter xdev for the estimated log-ratio is $$estxdev = estlratio/\delta_{estlratio}. \quad (27)$$

FIG. 28 shows an estimated ST log-ratio plot by Eq. 25. Real experimental data used in the plot is the same as that in FIG. 20.

To compare the performance of the two different estimation algorithms described by Eqs. 17 and 25, respectively, the ST log-ratio spread (standard deviation) in the high log-intensity (>0) side and in the low log-intensity (<0) side are especially of interest. At high intensity range, the log-ratio spread is about the same for both algorithms. At low intensity range, the ISEC algorithm has much smaller log-ratio spread than the algorithm as described by Eq. 25. In addition, many false up- or down-regulated signatures are shown at the low intensity range in FIG. 28. This indicates that the algorithm as described by Eq. 25 produces less accurate log-ratio estimations than the ISEC algorithm for those less bright spots. Table 1 summarizes the differences in performance based on seven sets of ST experiments.

TABLE 1

Comparison of Performance of Algorithms in 7 ST Virtual Experiment Data Sets

| algorithm | mean log-ratio standard deviation at high log-intensity (>0) | mean log-ratio standard deviation at low log-density (<0) | mean number of signatures |
|---|---|---|---|
| ISEC | 0.041 | 0.17 | 6 |
| Eqs. 25 | 0.047 | 0.65 | 233 |

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for generating an error-corrected differential profile A vs. B from sets of data A, B, CA, and CB, comprising
   (a) calculating a first differential profile A vs. B;
   (b) determining a systematic cross-experiment error by a method comprising calculating a reference differential profile CA vs. CB; and
   (c) generating a second differential profile A vs. B by a method comprising correcting said first differential profile A vs. B using said determined systematic cross-experiment error;
   wherein said data set A, B, CA or CB comprises respectively data set {A(i)}, {B(i)}, {CA(i)} or {CB(i)}, said data set {A(i)} representing measurements of a plurality of different cellular constituents measured in a sample having been subject to condition A, said data set {B(i)} representing measurements of said plurality of different cellular constituents measured in a sample having been subject to condition B, and said data sets {CA(i)} and {CB(i)} each representing measurements of said plurality of different cellular constituents measured in a sample having been subject to condition C, wherein i=1, 2, . . . , N is the index of measurements of cellular constituents, N being the total number of measurements; wherein data sets A and CA are measured in the same experimental reaction, and data sets B and CB are measured in the same experimental reaction; and wherein said second differential profile is taken as said error-corrected differential profile A vs. B.

2. The method of claim 1, wherein said first differential profile A vs. B comprises {log[(B(i)/A(i))]}, and said reference differential profile $C_A$ vs. $C_B$ comprises {log[$C_A$(i)/$C_B$(i)]}.

3. The method of claim 1, wherein said first differential profile A vs. B comprises {B(i)−A(i)}, and said reference differential profile $C_A$ vs. $C_B$ comprises {$C_A$(i)−$C_B$(i)}.

4. The method of claim 1, wherein said first differential profile A vs. B comprises {B(i)/A(i)}, and said reference differential profile $C_A$ vs. $C_B$ comprises {$C_A$(i)/$C_B$(i)}.

5. The method of claim 2, wherein said method of correcting said first differential profile comprising scaling said reference differential profile $C_A$ vs. $C_B$ by a scaling constant $\alpha$ and subtracting said scaled reference differential profile from said first differential profile A vs. B.

6. The method of claim 5, wherein said scaling constant a is determined by minimizing a function of the difference between said reference differential profile and said first differential profile.

7. The method of claim 6, wherein said function is described by equation $$\chi^2 = \frac{\sum_{i=1}^{N} \frac{(lratio\ (i) - \alpha \cdot stlratio\ (i))^2}{\sigma_{lratio}^2(i) + \sigma_{stlratio}^2(i)} \cdot w(i)}{\sum_{i=1}^{N} w(i)}$$

wherein $lratio(i)=\{\log[B(i)/A(i)]\}$ and $slratio(i)=\{\log[C_A(i)/C_B(i)]\}$, $\sigma_{lratio}(i)$ and $\sigma_{stlratio}(1)$ are standard deviations of said lratio(i) and stlratio(i), respectively, and w(i) is a weighting factor for cellular constituent i.

8. The method of claim 7, wherein said second differential profile A vs. B is calculated by equation $\log(B/A)(i)=w(i)\cdot(lratio(i)-\alpha\cdot stlratio(i))+(1-w(i))\cdot lratio(i).$ wherein said second differential profile A vs. B comprises $\{\log[(B/A)(i)]\}$.

9. The method of any one of claims 1–8, wherein said data sets $C_A$ and $C_B$ are measured using samples labeled with the same fluorophore.

10. The method of any one of claims 1–8, wherein said data sets CA and CB are measured using samples labeled with different fluorophores.

11. The method of any one of claims 1–8, wherein said sample having been subject to condition A and said sample having been subject to condition B are labeled with different fluorophores.

12. The method of any one of claims 1–8, wherein said sample having been subject to condition A is labeled with a first fluorophore and said sample having been subject to condition B is labeled with a second fluorophore, said second fluorophore being different from said first fluorophore.

13. The method of claim 12, further comprising determining an error-corrected fluor-reversed differential profile B vs. A from fluor-reversed data sets A and B, said fluor-reversed data sets A and B are measured when said sample having been subject to condition A is labeled with said second fluorophore and said sample having been subject to condition B is labeled with said first fluorophore.

14. The method of claim 13, further comprising combining said error-corrected differential profile A vs. B and said fluor-reversed error-corrected differential profile B vs. A to remove fluorophore bias.

15. The method of any one of claims 1–8, wherein said N is at least 50.

16. The method of claim 15, wherein said N is at least 100.

17. The method of claim 16, wherein said N is at least 1000.

18. The method of claim 17, wherein said N is at least 10,000.

19. A method for generating a differential profile A vs. B from data sets A and B, comprising
(a) determining mean background noise levels Abkg and Bbkg, and background noise residue ABres, from measured background noise levels in data sets A and B, respectively;

(b) calculating noise-removed data sets A and B, respectively, by a method comprising (b1) removing said mean background noise level from said data sets A and B, and (b2) removing said background noise residue from said data sets A and B, respectively; and (c) generating said differential profile A vs. B from said noise-removed data sets A and B;

wherein said data set A or B comprises respectively data set $\{A(i), A_{bkg}(i)\}$ or $\{B(i), B_{bkg}(i)\}$ representing measurements of a plurality of different cellular constituents in a sample, said sample having been subject to condition A or B, respectively; wherein $A_{bkg}(i)$ or $B_{bkg}(i)$ is said measured background noise level of measurement of cellular constituent i in said data set A or B, respectively; and wherein i=1, 2, . . . , N is the index of measurements of cellular constituents, N being the total number of measurements.

20. The method of claim 19, wherein said mean background noise level and said background noise residue in said data sets A and B are calculated according to equations $$Abkg = \frac{1}{N}\sum_{i=1}^{N} A_{bkg}(i)$$

$$Bbkg = \frac{1}{N}\sum_{i=1}^{N} B_{bkg}(i)$$

$$ABres = \left(\sum_i w(i)*(A(i)-Abkg)\right)\bigg/\left(\sum_i w(i)\right) - \left(\sum_j w(j)*(B(j)-Bbkg)\right)\bigg/\left(\sum_j w(j)\right)$$

wherein said w(i) is a window function.

21. The method of claim 20, wherein said noise-removed data sets A and B are calculated according to equations $\underline{A}(i)=Ai-Abkg-ABres$ if $ABres>0$ $\underline{B}(i)=Bi-Bbkg+ABres$ if $ABres<=0$ wherein said noise-removed data sets A and B comprises $\{\underline{A}(i)\}$ and $\{\underline{B}(i)\}$, respectively.

22. The method of claim 21, wherein said differential profile is calculated according to equation $xdev(i)=[\underline{A}(i)-\underline{B}(i)]/[sigma\_A^2+sigma\_B^2+f^{2*}(\underline{A}^2+\underline{B}^2)]^{1/2}$ wherein f is the fractional error ratio between the multiplicative noise and the signal intensity; and sigma_A and sigma_B are described according to equations $$sigma\ldots A = \sqrt{\frac{1}{N-1}\sum_{i=1}^{N}(A_{bkg}(i)-Abkg)^2}$$

$$sigma\ldots B = \sqrt{\frac{1}{N-1}\sum_{i=1}^{N}(B_{bkg}(i)-Bbkg)^2}$$

wherein said differential profile comprises $\{xdev(i)\}$.

23. The method of any one of claims 19–22, wherein said sample having been subject to condition A and said sample having been subject to condition B are labeled with the same fluorophore.

24. The method of any one of claims 19–22, wherein said sample having been subject to condition A is labeled with a first fluorophore and said sample having been subject to condition B is labeled with a second fluorophore, said second fluorophore being different from said first fluorophore.

25. The method of claim 24, further comprising determining a fluor-reversed differential profile B vs. A from a fluor-reversed data sets A and B, said fluor-reversed data sets A and B are measured when said sample having been subject to condition A is labeled with said second fluorophore and said sample having been subject to condition B is labeled with said first fluorophore.

26. The method of claim 25, further comprising combining said differential profile A vs. B and said fluor-reversed differential profile B vs. A to remove fluorophore bias.

27. The method of any one of claims 19–22, wherein said N is at least 50.

28. The method of claim 27, wherein said N is at least 100.

29. The method of claim 28, wherein said N is at least 1000.

30. The method of claim 29, wherein said N is at least 10,000.

31. A method for generating a differential profile A vs. B from data sets A and B measured in separate experimental reactions, comprising repeating the step of (b2) in any one of claims 19–22 a plurality of times.

32. The method of claim 31, wherein said plurality of times is at least 5 times.

33. The method of claim 32, wherein said plurality of times is at least 10 times.

34. The method of claim 33, wherein said plurality of times is at least 20 times.

35. The method of any one of claims 1–8 and 19–22, wherein said measurements of said plurality of different cellular constituents are expression levels of a plurality of nucleic acid species.

36. The method of claim 35, wherein said expression levels are measured using microarrays comprising a plurality of polynucleotide probes.

37. The method of any one of claims 1–8 and 19–22, wherein said measurements of said plurality of different cellular constituents are abundances of a plurality of protein species.

38. The method of claim 37, wherein said expression levels are measured using arrays comprising a plurality of antibody probes.

39. The method of claim 14, wherein said measurements of said plurality of different cellular constituents are expression levels of a plurality of nucleic acid species.

40. The method of claim 39, wherein said expression levels are measured using microarrays comprising a plurality of polynucleotide probes.

41. The method of claim 14, wherein said measurements of said plurality of different cellular constituents are abundances of a plurality of protein species.

42. The method of claim 41, wherein said expression levels are measured using arrays comprising a plurality of antibody probes.

43. A computer system for carrying out a method of generating a differential profile, said computer system comprising a processor, and a memory coupled to said processor and encoding one or more programs, wherein said one or more programs cause the processor to carry out the method of any one of the claims 1–8 and 19–22.

44. A computer system for carrying out a method of generating a differential profile, said computer system comprising a processor, and a memory coupled to said processor and encoding one or more programs, wherein said one or more programs cause the processor to carry out the method of claim 31.

45. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method of any one of the claims 1–8 and 19–22.

46. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method of claim 31.

* * * * *